United States Patent
Borthwick et al.

(10) Patent No.: US 7,235,544 B2
(45) Date of Patent: Jun. 26, 2007

(54) 3-SULFONYLAMINO-PYRROLIDINE-2-ONE DERIVATIVES AS INHIBITORS OF FACTOR XA

(75) Inventors: Alan David Borthwick, Stevenage (GB); John David Harling, Stevenage (GB); Wendy Rebecca Irving, Stevenage (GB); Savvas Kleanthous, Stevenage (GB); Nigel Stephen Watson, Stevenage (GB); Robert John Young, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 2 days.

(21) Appl. No.: 10/561,328

(22) PCT Filed: Jun. 17, 2004

(86) PCT No.: PCT/EP2004/006604

§ 371 (c)(1),
(2), (4) Date: Dec. 19, 2005

(87) PCT Pub. No.: WO2004/110997

PCT Pub. Date: Dec. 23, 2004

(65) Prior Publication Data

US 2006/0178419 A1    Aug. 10, 2006

(30) Foreign Application Priority Data

Jun. 19, 2003  (GB) .................................. 0314369.0
Mar. 15, 2004  (GB) .................................. 0405774.1

(51) Int. Cl.
| A61K 31/5377 | (2006.01) |
| A61K 31/381 | (2006.01) |
| A61K 31/397 | (2006.01) |
| A61K 31/402 | (2006.01) |
| C07D 411/10 | (2006.01) |
| C07D 401/10 | (2006.01) |
| C07D 207/12 | (2006.01) |

(52) U.S. Cl. ............................. 514/210.2; 514/235.5; 514/326; 514/343; 514/422; 544/141; 548/518; 548/527; 548/530; 548/578; 548/950; 546/207; 546/208

(58) Field of Classification Search ................ 544/141; 546/207, 208; 548/518, 527, 530, 578, 950; 514/210.2, 235.5, 326, 343, 422, 423

See application file for complete search history.

(56) References Cited

U.S. PATENT DOCUMENTS

| 5,731,315 A | 3/1998 | Ewing et al. |
| 5,958,918 A | 9/1999 | Choi-Sledeski et al. |
| 6,034,093 A | 3/2000 | Ewing et al. |
| 6,348,600 B1 | 2/2002 | Ono et al. |
| 2002/0183324 A1 | 12/2002 | Jacobson et al. |

FOREIGN PATENT DOCUMENTS

| WO | 92/10476 | 6/1992 |
| WO | 97/43257 | 11/1997 |
| WO | 98/24784 | 6/1998 |
| WO | 2002/002519 | 1/2002 |
| WO | 2002/032897 | 4/2002 |
| WO | 2002/080853 | 10/2002 |
| WO | 03/043981 | 5/2003 |
| WO | 03/053925 | 7/2003 |

*Primary Examiner*—Kamal Saeed
*Assistant Examiner*—Karen Cheng
(74) *Attorney, Agent, or Firm*—Jennifer L. Fox

(57) ABSTRACT

The invention relates to compounds of formula (I):

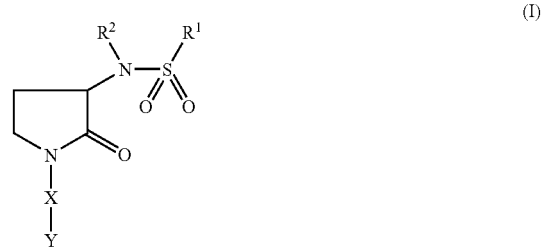

wherein substituents are as defined.

8 Claims, No Drawings

3-SULFONYLAMINO-PYRROLIDINE-2-ONE DERIVATIVES AS INHIBITORS OF FACTOR XA

This application is filed pursuant to 35 U.S.C. § 371 as a United States National Phase Application of International Application No. PCT1EP2004/006604 filed Jun. 17, 2004, which claims priority from GB 0314369.0 filed Jun. 19, 2003 and GB 0405774.1 filed Mar. 15, 2004.

FIELD OF THE INVENTION

The present invention relates to a novel class of chemical compounds, to processes for their preparation, to pharmaceutical compositions containing them and to their use in medicine, particularly use in the amelioration of a clinical condition for which a Factor Xa inhibitor is indicated.

BACKGROUND OF THE INVENTION

Factor Xa is a member of the trypsin-like serine protease class of enzymes. It is a key enzyme in the coagulation cascade. A one-to-one binding of Factors Xa and Va with calcium ions and phospholipid converts prothrombin into thrombin. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure. Beyond its direct role in the formation of fibrin rich blood clots, thrombin has been reported to have profound bioregulatory effects on a number of cellular components within the vasculature and blood, (Shuman, M. A., Ann. NY Acad. Sci., 405: 349 (1986)).

A Factor Xa inhibitor may be useful in the treatment of acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke. Factor Xa inhibitors may also be useful in preventing thrombosis and complications in patients genetically predisposed to arterial thrombosis or venous thrombosis and patients that have a disease-associated predisposition to thrombosis (e.g. type 2 diabetics). Thrombin has been reported to contribute to lung fibroblast proliferation, thus, Factor Xa inhibitors could be useful for the treatment of some pulmonary fibrotic diseases. Factor Xa inhibitors could also be useful in the treatment of tumour metastasis, by suppressing coagulation and thus preventing fibrin deposition and its concommittant facilitation of metastasis. A Factor Xa inhibitor may also have utility as an anti-inflammatory agent through its inhibition of FXa mediated activation of protease-activated receptors (PARs 1 and 2). A Factor Xa inhibitor may also have utility as an anti-atherosclerotic agent through the suppression of platelet-activation. Thrombin can induce neurite retraction and thus Factor Xa inhibitors may have potential in neurogenerative diseases such as Parkinson's and Alzheimer's disease. Factor Xa inhibitors may also have utility as anticoagulant agents in connection with the preparation, storage, fractionation or use of whole blood. They have also been reported for use in conjunction with thrombolytic agents, thus permitting the use of a lower dose of thrombolytic agent.

DESCRIPTION OF THE INVENTION

The present invention provides compounds of formula (I):

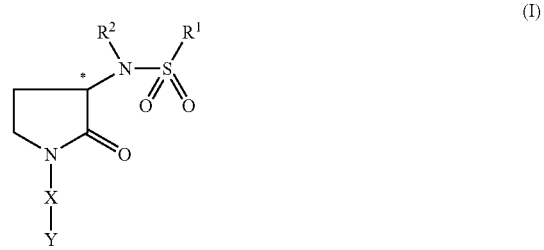

wherein:
$R^1$ represents a group selected from:

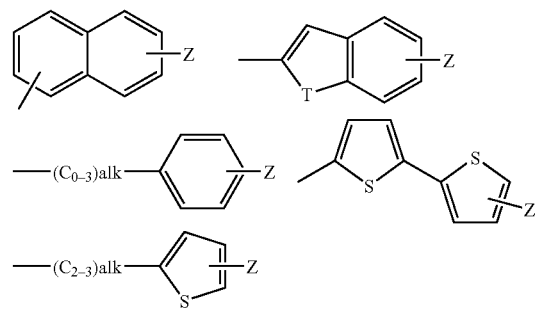

each ring of which optionally contains a further heteroatom N,
Z represents an optional substituent halogen,
alk represents alkylene or alkenylene,
T represents S, O or NH;
$R^2$ represents hydrogen, —$C_{1-6}$alkyl, —$C_{1-3}$alkylCON$R^aR^b$, —$C_{1-3}$alkylCO$_2C_{1-4}$alkyl, —CO$_2C_{1-4}$alkyl or —$C_{1-3}$alkylCO$_2$H;

$R^a$ and $R^b$ independently represent hydrogen, —$C_{1-6}$alkyl, or together with the N atom to which they are bonded form a 5-, 6- or 7-membered non-aromatic heterocyclic ring optionally containing an additional heteroatom selected from O, N and S, optionally substituted by $C_{1-4}$alkyl, and optionally the S heteroatom is substituted by O, i.e. represents $S(O)_n$;

n represents 0–2;

X represents phenyl or a 5- or 6-membered aromatic heterocyclic group containing at least one heteroatom selected from O, N or S, each of which is optionally substituted by 0–2 groups selected from: halogen, —$C_{1-4}$alkyl, —$C_{2-4}$alkenyl, —CN, —$CF_3$, —$NR^aR^b$, —$C_{0-4}$alkyl$OR^e$, —$C(O)R^f$ and —$C(O)NR^aR^b$;

$R^e$ represents hydrogen or —$C_{1-6}$alkyl;

$R^f$ represents —$C_{1-6}$alkyl;

Y represents a group —$C(R^x)(R^z)C_{0-2}$alkyl$NR^cR^d$;

$R^x$ represents $C_{1-4}$alkyl optionally substituted by halogen (e.g. $CF_3$, —$CH_2CF_3$);

$R^z$ represents hydrogen or $C_{1-4}$alkyl optionally substituted by halogen (e.g. $CF_3$, —$CH_2CF_3$);

$R^c$ and $R^d$ independently represent hydrogen, —$C_{1-6}$alkyl, —$C_{1-4}$alkylOH, or together with the N atom to which they are bonded form a 4-, 5-, 6- or 7-membered non-aromatic heterocyclic ring, the 5-, 6- or 7-membered non-aromatic heterocyclic ring optionally containing an additional heteroatom selected from O, N or S, optionally substituted by $C_{1-4}$alkyl;

and/or pharmaceutically acceptable derivative thereof.

Further aspects of the invention are:
  A pharmaceutical composition comprising a compound of the invention together with a pharmaceutical carrier and/or excipient.
  A compound of the invention for use in therapy.
  Use of a compound of the invention for the manufacture of a medicament for the treatment of a patient suffering from a condition susceptible to amelioration by a Factor Xa inhibitor.
  A method of treating a patient suffering from a condition susceptible to amelioration by a Factor Xa inhibitor comprising administering a therapeutically effective amount of a compound of the invention.

In one aspect of the invention, the present invention provides compounds of formula (I):

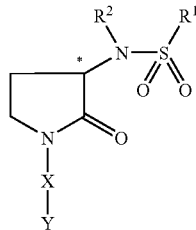

(I)

wherein:
$R^1$ represents a group selected from:

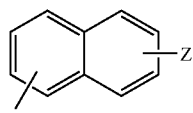 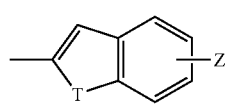

-continued

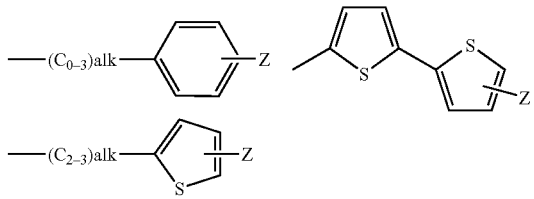

each ring of which optionally contains a further heteroatom N,

Z represents an optional substituent halogen, alk represents alkylene or alkenylene, T represents S, O or NH;

$R^2$ represents hydrogen, —$C_{1-6}$alkyl, —$C_{1-3}$alkylCON$R^aR^b$, —$C_{1-3}$alkyl$CO_2C_{1-4}$alkyl, —$CO_2C_{1-4}$alkyl or —$C_{1-3}$alkyl$CO_2H$;

$R^a$ and $R^b$ independently represent hydrogen, —$C_{1-6}$alkyl, or together with the N atom to which they are bonded form a 5-, 6- or 7-membered non-aromatic heterocyclic ring optionally containing an additional heteroatom selected from O, N or S, optionally substituted by $C_{1-4}$alkyl, and optionally the S heteroatom is substituted by O, i.e. represents $S(O)_n$;

X represents phenyl or a 5- or 6-membered aromatic heterocyclic group containing at least one heteroatom selected from O, N or S, each of which is optionally substituted by 0–2 groups selected from: halogen, —$C_{1-4}$alkyl, —$C_{2-4}$alkenyl, —CN, —$CF_3$, —$NR^aR^b$, —$C_{0-4}$alkyl$OR^e$, —$C(O)R^f$ and —$C(O)NR^aR^b$;

$R^e$ represents hydrogen or —$C_{1-6}$alkyl;

$R^f$ represents —$C_{1-6}$alkyl;

Y represents a group —$C(R^x)(R^z)C_{0-2}$alkyl$NR^cR^d$;

$R^x$ represents $C_{1-4}$alkyl optionally substituted by halogen (e.g. $CF_3$, —$CH_2CF_3$);

$R^z$ represents hydrogen or $C_{1-4}$alkyl optionally substituted by halogen (e.g. $CF_3$, —$CH_2CF_3$);

$R^c$ and $R^d$ independently represent hydrogen, —$C_{1-6}$alkyl, —$C_{1-4}$alkylOH, or together with the N atom to which they are bonded form a 5- or 6-membered non-aromatic heterocyclic ring optionally containing an additional heteroatom selected from O, N or S, optionally substituted by $C_{1-4}$alkyl;

and pharmaceutically acceptable derivatives thereof.

In one aspect of the invention, $R^1$ represents a group selected from:

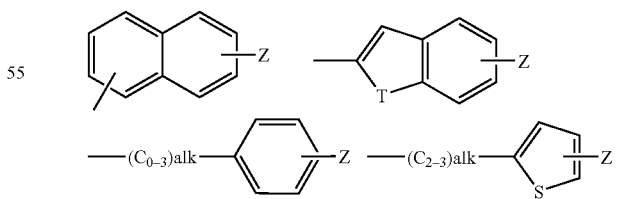

each ring of which optionally contains a further heteroatom N,

Z represents an optional substituent halogen, alk represents alkylene or alkenylene, T represents S, O or NH.

In another aspect, $R^1$ represents a group selected from:

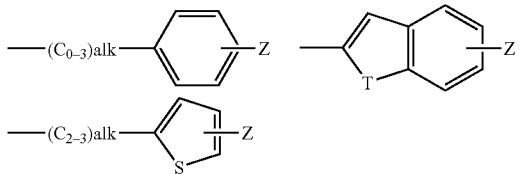

each ring of which optionally contains a further heteroatom N,
Z represents an optional substituent halogen,
alk represents alkylene or alkenylene,
T represents S, O or NH.

In another aspect, $R^1$ represents a group selected from:

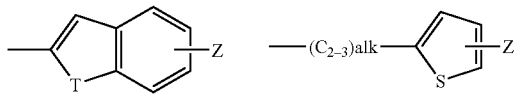

Z represents an optional substituent halogen,
alk represents alkylene or alkenylene,
T represents S, O or NH.

Alternatively, $R^1$ represents a group selected from:

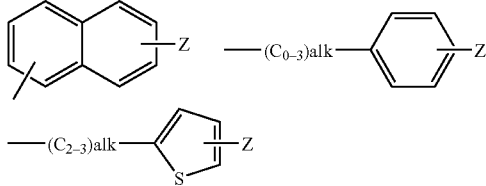

each ring of which optionally contains a further heteroatom N,
Z represents an optional substituent halogen,
alk represents alkylene or alkenylene.

Alternatively, $R^1$ represents a group selected from:

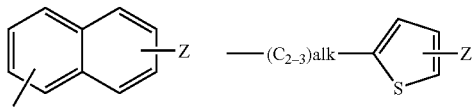

each ring of which optionally contains a further heteroatom N,
Z represents an optional substituent halogen,
alk represents alkylene or alkenylene.

In another aspect, $R^1$ represents a group selected from:

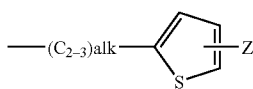

Z represents an optional substituent halogen,
alk represents alkylene or alkenylene.

Alternatively, $R^1$ represents a group selected from:

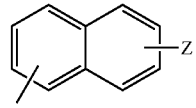

Z represents an optional substituent halogen.

In one aspect of the invention, T represents S.
In one aspect of the invention, $R^2$ represents hydrogen.
In one aspect of the invention, $R^a$ and $R^b$ independently represent hydrogen or —$C_{1-6}$alkyl.
In one aspect of the invention, n represents 0–2.
In one aspect of the invention, X represents phenyl or a 5- or 6-membered aromatic heterocyclic group containing at least one heteroatom selected from O, N or S, each of which is optionally substituted by 0–2 groups selected from: halogen, —$C_{1-4}$alkyl and —$NR^aR^b$. In another aspect, X represents phenyl which is optionally substituted by 0–2 groups selected from: halogen, —$C_{1-4}$alkyl and —$NR^aR^b$. In another aspect, X represents phenyl substituted by 0–2 halogen groups. In another aspect, X represents phenyl substituted by 1–2 halogen groups. In another aspect, X represents phenyl substituted by a halogen. In another aspect, X represents phenyl substituted by a fluorine.

In one aspect of the invention, Y represents a group —$C(R^x)(R^z)NR^cR^d$. In another aspect, Y represents a group —$C_{2-3}$alkyl$NR^cR^d$. In another aspect, Y represents —$C(CH_3)$—$NR^cR^d$.

In one aspect of the invention, $R^x$ represents $C_{1-4}$alkyl. In another aspect, $R^x$ represents methyl.

In one aspect of the invention $R^z$ represents hydrogen or $C_{1-4}$alkyl. In another aspect, $R^z$ represents hydrogen or methyl. In another aspect, $R^z$ represents hydrogen.

In one aspect of the invention, $R^c$ and $R^d$ independently represent hydrogen, —$C_{1-6}$alkyl, —$C_{1-4}$alkylOH, or together with the N atom to which they are bonded form a 4-, 5- or 6-membered non-aromatic heterocyclic ring, the 5- or 6-membered non-aromatic heterocyclic ring optionally containing an additional heteroatom selected from O, N or S, optionally substituted by $C_{1-4}$alkyl. In another aspect of the invention, $R^c$ and $R^d$ independently represent hydrogen, —$C_{1-4}$alkyl, —$C_{1-4}$alkylOH, or together with the N atom to which they are bonded form a 4-, 5- or 6-membered non-aromatic heterocyclic ring, the 5- or 6-membered non-aromatic heterocyclic ring optionally containing an additional heteroatom selected from O, N or S. In another aspect of the invention, $R^c$ and $R^d$ independently represent hydrogen, —$C_{1-4}$alkyl, —$C_{1-4}$alkylOH, or together with the N atom to which they are bonded form a 6-membered non-aromatic heterocyclic ring optionally containing an additional heteroatom selected from O, N and S. In another aspect, $R^c$ represents methyl and $R^d$ represents —$C_{1-4}$alkyl or —$C_{1-4}$alkylOH, or $R^c$ and $R^d$ together with the N atom to which they are bonded form a 6-membered non-aromatic heterocyclic ring optionally containing an additional heteroatom selected from O, N and S. In another aspect, $R^c$ represents methyl and $R^d$ represents —$C_{1-4}$alkyl or —$C_{1-4}$alkylOH, or $R^c$ and $R^d$ together with the N atom to which they are bonded form a morpholino ring. In another aspect of the invention, $R^c$ and $R^d$ independently represent hydrogen, —$C_{1-4}$alkyl, or together with the N atom to which they are bonded form a 4-, 5- or 6-membered non-aromatic heterocyclic ring. In another aspect of the invention, $R^c$ and $R^d$ together with the N atom to which they are bonded form a 4-, 5- or 6-membered non-aromatic heterocyclic ring, e.g. azetidine. In another aspect of the invention, $R^c$ and $R^d$ independently represent hydrogen or —$C_{1-4}$alkyl. In another aspect of the invention, $R^c$ represents —$C_{1-4}$alkyl and $R^d$ represents hydrogen. In another aspect, $R^c$ and $R^d$ both represent methyl. It is to be understood that the above-mentioned optional substituent $C_{1-4}$alkyl may be on the 4-, 5-, 6- or 7-membered non-aromatic ring of $R^c$ and $R^d$.

It is to be understood that the present invention covers all combinations of the various aspects of the invention described herein above.

As used herein, the term "alkyl" means both straight and branched chain saturated hydrocarbon groups. Examples of alkyl groups include methyl (—$CH_3$), ethyl (—$C_2H_5$), propyl (—$C_3H_7$) and butyl (—$C_4H_9$).

As used herein, the term "alkylene" means both straight and branched chain saturated hydrocarbon linker groups. Examples of alkylene groups include methylene (—$CH_2$—), ethylene (—$CH_2CH_2$—) and propylene (—$CH_2CH_2CH_2$—).

As used herein, the term "alkenylene" means both straight and branched chain unsaturated hydrocarbon linker groups, wherein the unsaturation is present only as double bonds. Examples of alkenylene groups includes ethenylene (—CH═CH—) and propenylene (—$CH_2$—CH═CH—).

As used herein, the term "heterocyclic group" means optionally substituted rings containing one or more heteroatoms selected from: nitrogen, sulphur and oxygen atoms. The heterocycle may be aromatic or non-aromatic, i.e., may be saturated, partially or fully unsaturated. Examples of 5-membered groups include thienyl, furanyl, pyrrolidinyl thiazolyl, oxazolyl and imidazolyl. Examples of 6-membered groups include pyridyl, piperidinyl, pyrimidinyl and morpholinyl. Examples of 7-membered groups include hexamethyleneiminyl. Certain heterocyclic groups, e.g. thienyl, furanyl, thiazolyl, oxazolyl, pyridyl and pyrimidinyl are C-linked to the rest of the molecule. Other heterocyclic groups, e.g pyrrolidinyl, imidazolyl, piperidyl, morpholinyl and hexamethyleneiminyl may be C-linked or N-linked to the rest of the molecule.

As used herein, the term "halogen" means an atom selected from fluorine, chlorine, bromine and iodine.

As used herein, the term "pharmaceutically acceptable" means a compound which is suitable for pharmaceutical use.

As used herein, the term "pharmaceutically acceptable derivative", means any pharmaceutically acceptable salt, solvate, or prodrug e.g. ester or carbamate, or salt or solvate of such a prodrug, of a compound of formula (I), which upon administration to the recipient is capable of providing (directly or indirectly) a compound of formula (I), or an active metabolite or residue thereof. Exemplary pharmaceutically acceptable derivatives are salts, solvates, esters and carbamates. More exemplary pharmaceutically acceptable derivatives are salts, solvates and esters. Even more exemplary pharmaceutically acceptable derivatives are salts and solvates.

Suitable salts according to the invention may include those formed with both organic and inorganic acids and bases. Pharmaceutically acceptable acid addition salts include those formed from mineral acids such as: hydrochloric, hydrobromic, sulphuric, phosphoric, acid; and organic acids such as: citric, tartaric, lactic, pyruvic, acetic, trifluoroacetic, succinic, oxalic, formic, fumaric, maleic, oxaloacetic, methanesulphonic, ethanesulphonic, p-toluenesulphonic, benzenesulphonic and isethionic acids. Exemplary pharmaceutically acceptable salts include those formed from hydrochloric, trifluoroacetic and formic acids. Thus, in one aspect of the invention pharmaceutically acceptable salts are formic acid salts.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of formula (I) are within the scope of the invention.

Salts and solvates of compounds of formula (I) which are suitable for use in medicine may be those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and their pharmaceutically acceptable salts and solvates.

The compounds of formula (I) contain chiral (asymmetric) centres. The individual stereoisomers (enantiomers and diastereoisomers) and mixtures of these are within the scope of the present invention. In one aspect of the invention, the stereochemistry is (S) at the 3-position on the 2-oxopyrrolidine ring (as indicated by the symbol *)

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115–130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved in vivo yielding the parent compound. Prodrugs may include, for example, compounds of this invention wherein hydroxyl or amine groups are bonded to any group that, when administered to a patient, cleaves to form the hydroxyl or amine groups.

Esters may be active in their own right and/or be hydrolysable under in vivo conditions in the human body. Suitable pharmaceutically acceptable in vivo hydrolysable ester groups include those which break down readily in the human body to leave the parent acid or its salt. An ester may be formed at a carboxylic acid (—COOH) group or a hydroxyl (—OH) group, by methods well known in the art involving reaction with the corresponding alcohol, acid, acid chloride, anhydride, or amide. For example, esters may be $C_{1-6}$alkyl esters, e.g. methyl esters, ethyl esters, and the like.

Exemplary compounds of the invention include:

(E)-2-(5-Chloro-2-thienyl)-N-(1-{4-[1-(dimethylamino)ethyl]-2-fluorophenyl}-2-oxo-3-pyrrolidinyl)ethenesulfonamide;

(E)-2-(5-Chloro-2-thienyl)-N-(1-{2-fluoro-4-[1-(4-morpholinyl)ethyl]phenyl}-2-oxo-3-pyrrolidinyl)ethenesulfonamide;

(E)-2-(5-Chloro-2-thienyl)-N-[1-(2-fluoro-4-{1-[(2-hydroxyethyl)(methyl)amino]ethyl}phenyl)-2-oxo-3-pyrrolidinyl]ethenesulfonamide;

(E)-N-{1-[4-(1-Aminoethyl)-2-fluorophenyl]-2-oxo-3-pyrrolidinyl}-2-(5-chloro-2-thienyl)ethenesulfonamide;
6-Chloro-N-(1-{4-[1-(dimethylamino)ethyl]-2-fluorophenyl}-2-oxo-3-pyrrolidinyl)-1-benzothiophene-2-sulfonamide;
(E)-2-(5-Chloro-2-thienyl)-N-((3S)-1-{4-[(1S)-1-(dimethylamino)ethyl]-2-fluorophenyl}-2-oxo-3-pyrrolidinyl)ethenesulfonamide;
6-Chloro-N-((3S)-1-{4-[(1S)-1-(dimethylamino)ethyl]-2-fluorophenyl}-2-oxo-3-pyrrolidinyl)-2-naphthalenesulfonamide;
6-Chloro-N-((3S)-1-{4-[(1S)-1-(dimethylamino)ethyl]-2-fluorophenyl}-2-oxo-3-pyrrolidinyl)-1-benzothiophene-2-sulfonamide;
(E)-2-(5-Chloro-2-thienyl)-N-((3S)-1-{4-[(1R)-1-(dimethylamino)ethyl]-2-fluorophenyl}-2-oxo-3-pyrrolidinyl)ethenesulfonamide;
6-Chloro-N-((3S)-1-{4-[(1R)-1-(dimethylamino)ethyl]-2-fluorophenyl}-2-oxo-3-pyrrolidinyl)-2-naphthalenesulfonamide;
6-Chloro-N-((3S)-1-{4-[(1R)-1-(dimethylamino)ethyl]-2-fluorophenyl}-2-oxo-3-pyrrolidinyl)-1-benzothiophene-2-sulfonamide;
(E)-2-(5-Chloro-2-thienyl)-N-((3S)-1-{4-[(1R)-1-(dimethylamino)ethyl]-2,6-difluorophenyl}-2-oxo-3-pyrrolidinyl)ethenesulfonamide;
(E)-2-(5-Chloro-2-thienyl)-N-((3S)-1-{4-[(1S)-1-(dimethylamino)ethyl]-2,6-difluorophenyl}-2-oxo-3-pyrrolidinyl)ethenesulfonamide;
(E)-2-(5-Chloro-2-thienyl)-N-((3S)-1-{4-[1-(dimethylamino)propyl]-2-fluorophenyl}-2-oxo-3-pyrrolidinyl)ethenesulfonamide;
(E)-2-(5-Chloro-2-thienyl)-N-((3S)-1-{4-[1-(dimethylamino)-2-methylpropyl]-2-fluorophenyl}-2-oxo-3-pyrrolidinyl)ethenesulfonamide;
(E)-2-(5-Chloro-2-thienyl)-N-(1-{4-[1-(dimethylamino)-1-methylethyl]-2-fluorophenyl}-2-oxo-3-pyrrolidinyl)ethenesulfonamide;
6-Chloro-N-(1-{4-[1-(dimethylamino)-1-methylethyl]-2-fluorophenyl}-2-oxo-3-pyrrolidinyl)-2-naphthalenesulfonamide;
6-Chloro-N-(1-{4-[1-(dimethylamino)-1-methylethyl]-2-fluorophenyl}-2-oxo-3-pyrrolidinyl)-1-benzothiophene-2-sulfonamide;
6-Chloro-N-(1-{4-[1-(dimethylamino)ethyl]-2-fluorophenyl}-2-oxo-3-pyrrolidinyl)-2-naphthalenesulfonamide;
6-Chloro-N-(1-{4-[1-(ethylamino)ethyl]-2-fluorophenyl}-2-oxo-3-pyrrolidinyl)-2-naphthalenesulfonamide;
6-Chloro-N-[1-(4-{1-[ethyl(methyl)amino]ethyl}-2-fluorophenyl)-2-oxo-3-pyrrolidinyl]-2-naphthalenesulfonamide;
6-Chloro-N-[1-(2-fluoro-4-{1-[(1-methylethyl)amino]ethyl}phenyl)-2-oxo-3-pyrrolidinyl]-2-naphthalenesulfonamide;
6-Chloro-N-[1-(2-fluoro-4-{1-[methyl(1-methylethyl)amino]ethyl}phenyl)-2-oxo-3-pyrrolidinyl]-2-naphthalenesulfonamide;
N-(1-{4-[1-(1-Azetidinyl)ethyl]-2-fluorophenyl}-2-oxo-3-pyrrolidinyl)-6-chloro-2-naphthalenesulfonamide;
6-Chloro-N-(1-{2-fluoro-4-[1-(1-pyrrolidinyl)ethyl]phenyl}-2-oxo-3-pyrrolidinyl)-2-naphthalenesulfonamide;
6-Chloro-N-(1-{2-fluoro-4-[1-(1-piperidinyl)ethyl]phenyl}-2-oxo-3-pyrrolidinyl)-2-naphthalenesulfonamide;
5'-Chloro-N-((3S)-1-{4-[1-(dimethylamino)ethyl]-2-fluorophenyl}-2-oxo-3-pyrrolidinyl)-2,2'-bithiophene-5-sulfonamide;
(E)-2-(5-Chloro-2-thienyl)-N-((3S)-1-{4-[(1S)-1-(dimethylamino)ethyl]phenyl}-2-oxo-3-pyrrolidinyl)ethenesulfonamide;
(E)-2-(5-Chloro-2-thienyl)-N-((3S)-1-{4-[(1R)-1-(dimethylamino)ethyl]phenyl}-2-oxo-3-pyrrolidinyl)ethenesulfonamide;
6-Chloro-N-((3S)-1-{4-[(1S)-1-(dimethylamino)ethyl]phenyl}-2-oxo-3-pyrrolidinyl)-1-benzothiophene-2-sulfonamide;
6-Chloro-N-((3S)-1-{4-[(1R)-1-(dimethylamino)ethyl]phenyl}-2-oxo-3-pyrrolidinyl)-1-benzothiophene-2-sulfonamide;
(1E)-2-(5-Chloro-2-thienyl)-N-(1-{4-[1-(dimethylamino)ethyl]-2,6-difluorophenyl}-2-oxo-3-pyrrolidinyl)-1-propene-1-sulfonamide; and
6-Chloro-N-(1-{4-[1-(dimethylamino)ethyl]-2,6-difluorophenyl}-2-oxo-3-pyrrolidinyl)-1-benzothiophene-2-sulfonamide.

Compounds of the invention may show advantageous properties, they may be more efficacious, may show greater selectivity, may have fewer side effects, may have a longer duration of action, may be more bioavailable by the preferred route, or may have other more desirable properties than similar known compounds.

The compounds of formula (I) are Factor Xa inhibitors and as such are useful in the treatment of clinical conditions susceptible to amelioration by administration of a Factor Xa inhibitor. Such conditions may include acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty (PTCA), transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke; in preventing thrombosis and complications in patients genetically predisposed to arterial thrombosis or venous thrombosis and patients that have a disease-associated predisposition to thrombosis (e.g. type 2 diabetics); the treatment of pulmonary fibrosis; the treatment of tumour metastasis; inflammation; atherosclerosis; neurogenerative disease such as Parkinson's and Alzheimer's diseases; Kasabach Merritt Syndrome; Haemolytic uremic syndrome; endothelial dysfunction; as anti-coagulants for extracorporeal blood in for example, dialysis, blood filtration, bypass, and blood product storage; and in the coating of invasive devices such as prostheses, artificial valves and catheters in reducing the risk of thrombus formation.

Accordingly, one aspect of the present invention provides a compound of formula (I) and/or a pharmaceutically acceptable derivative thereof for use in medical therapy, for example, for use in the amelioration of a clinical condition in a mammal, including a human, for which a Factor Xa inhibitor is indicated.

In another aspect, the invention provides a method for the treatment and/or prophylaxis of a condition susceptible to amelioration by a Factor Xa inhibitor in a mammal, including a human, which method comprises administering to the subject an effective amount of a compound of formula (I) or a pharmaceutically acceptable derivative thereof.

In another aspect, the present invention provides the use of a compound of formula (I) and/or a pharmaceutically acceptable derivative thereof, for the manufacture of a medicament for the treatment and/or prophylaxis of a condition susceptible to amelioration by a Factor Xa inhibitor.

In one aspect of the invention, the condition susceptible to amelioration by a Factor Xa inhibitor is selected from treatment of acute vascular diseases such as acute coronary syndromes (for example primary and secondary prevention of myocardial infarction and unstable angina and treatment of prothrombotic sequalae associated with myocardial infarction or heart failure), thromboembolism, acute vessel closure associated with thrombolytic therapy and percutaneous transluminal coronary angioplasty, transient ischemic attacks, pulmonary embolism, deep vein thrombosis, peripheral arterial occlusion, prevention of vessel luminal narrowing (restenosis), and the prevention of thromboembolic events associated with atrial fibrillation, e.g. stroke.

In another aspect, the condition susceptible to amelioration by a Factor Xa inhibitor is selected from acute coronary syndromes (for example primary and secondary prevention of myocardial infarction and unstable angina and treatment of prothrombotic sequalae associated with myocardial infarction or heart failure), pulmonary embolism, deep vein thrombosis and the prevention of thromboembolic events associated with atrial fibrillation, e.g. stroke.

It will be appreciated that reference to treatment includes acute treatment or prophylaxis as well as the alleviation of established symptoms.

While it is possible that, for use in therapy, a compound of the present invention may be administered as the raw chemical, the active ingredient may also be presented as a pharmaceutical formulation.

In a further aspect, the invention provides a pharmaceutical composition comprising at least one compound of formula (I) and/or a pharmaceutically acceptable derivative thereof in association with at least one pharmaceutically acceptable carrier and/or excipient. The carrier and/or excipient must be "acceptable" in the sense of being compatible with the other ingredients of the formulation and not deleterious to the recipient thereof.

In another aspect, the invention provides a pharmaceutical composition comprising, as active ingredient, at least one compound of formula (I) and/or a pharmaceutically acceptable derivative thereof in association with a pharmaceutically acceptable carrier and/or excipient for use in therapy, and for example in the treatment of human or animal subjects suffering from a condition susceptible to amelioration by a Factor Xa inhibitor.

There is further provided by the present invention a process of preparing a pharmaceutical composition, which process comprises mixing at least one compound of formula (I) and/or a pharmaceutically acceptable derivative thereof, together with at least one pharmaceutically acceptable carrier and/or excipient.

The compounds for use according to the present invention may be formulated for oral, buccal, parenteral, topical, rectal or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions or they may be presented as a dry product for constitution with water or other suitable vehicles before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled/extended release of the active compound.

For buccal administration the compositions may take the form of tablets or lozenges formulated in a conventional manner.

The compounds according to the present invention may be formulated for parenteral administration by injection, e.g. by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator.

Powders for external application may be formed with the aid of any suitable powder base, for example, lactose, talc or starch. Spray compositions may be formulated as aqueous solutions or suspensions or as aerosols delivered from pressurised packs, such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins or as sparingly soluble derivatives, for example, as a sparingly soluble salt.

A proposed dose of the compounds according to the present invention for administration to a human (of approximately 70 kg body weight) is 0.1 mg to 1 g, such as 1 mg to 500 mg of the active ingredient per unit dose, expressed as the weight of free base. The unit dose may be administered, for example, 1 to 4 times per day. It will be appreciated that it may be necessary to make routine variations to the dosage depending on the age and weight of the patient as well as the severity of the condition to be treated. The dosage may also depend on the route of administration. The precise dose and route of administration will ultimately be at the discretion of the attendant physician or veterinarian.

The compounds of formula (I) may also be used in combination with other therapeutic agents. The invention thus provides, in a further aspect, a combination comprising at least one compound of formula (I) and/or a pharmaceutically acceptable derivative thereof together with one or more further therapeutic agent(s).

When a compound of formula (I) and/or a pharmaceutically acceptable derivative thereof is used in combination with a second therapeutic agent the dose of each compound may differ from that when the compound is used alone. Appropriate doses will be readily appreciated by those skilled in the art. It will be appreciated that the amount of a compound of the invention required for use in treatment will vary with the nature of the condition being treated and the age and the condition of the patient and will be ultimately at the discretion of the attendant physician or veterinarian. The compounds of the present invention may be used in combination with other antithrombotic drugs (such as thrombin inhibitors, thromboxane receptor antagonists, prostacyclin mimetics, phosphodiesterase inhibitors, fibrinogen antagonists, thrombolytic drugs such as tissue plasminogen activator and streptokinase, non-steroidal anti-inflammatory drugs such as aspirin, and the like), anti-hypertensive agents (such as angiotensin-converting enzyme inhibitors, angiotensin-II receptor antagonists, ACE/NEP inhibitors, β-blockers, calcium channel blockers, PDE inhibitors, aldosterone blockers), anti-atherosclerotic/dyslipidaemic agents (such as HMG-CoA reductase inhibitors) and anti-arrhythmic agents.

The combinations referred to above may conveniently be presented for use in the form of a pharmaceutical formulation and thus pharmaceutical formulations comprising a combination as defined above together with at least one pharmaceutically acceptable carrier and/or excipient comprise a further aspect of the invention. The individual components of such combinations may be administered either sequentially or simultaneously in separate or combined pharmaceutical formulations by any convenient route.

When administration is sequential, either the Factor Xa inhibitor or the second therapeutic agent may be administered first. When administration is simultaneous, the combination may be administered either in the same or different pharmaceutical composition.

When combined in the same formulation it will be appreciated that the two compounds must be stable and compatible with each other and the other components of the formulation. When formulated separately they may be provided in any convenient formulation, conveniently in such manner as are known for such compounds in the art.

The compounds of formula (I) and/or pharmaceutically acceptable derivatives thereof may be prepared by the processes described hereinafter, said processes constituting a further aspect of the invention. In the following description, the groups are as defined above for compounds of formula (I) unless otherwise stated.

According to a further aspect of the present invention, there is provided a process (A) for preparing compounds of formula (I) which comprises of reacting compounds of formula (II) or an acid addition salt thereof with compounds of formula (III) where V is a suitable leaving group, such as a halide, e.g. chloride. When the free base of a compound of formula (II) is used, the reaction is conveniently carried out in the presence of a base, e.g. pyridine, and in a suitable solvent, e.g. acetonitrile (MeCN), suitably at 0° C. to room temperature. When the acid addition salt of a compound of formula (II) is used, the reaction is conveniently carried out in the presence of a base, e.g. N,N-diisopropylethylamine (DIPEA), and in a suitable solvent, e.g. MeCN, suitably at 0° C. to room temperature.

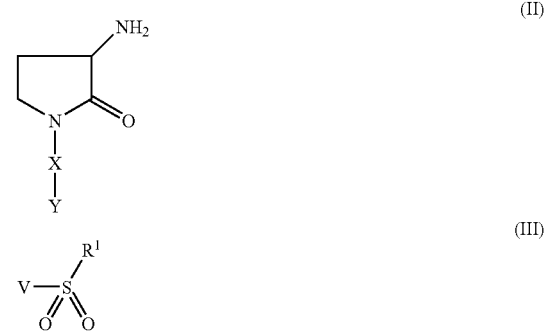

If X-Y contains a group reactive to compounds of formula (III), such groups may be protected prior to reaction of a compound of formula (II) with compounds of formula (III) using methods well known in the art and such protecting groups removed under standard conditions to provide compounds of formula (I) after completion of the reaction of compounds of formula (II) with compounds of formula (III).

Compounds of formula (III) are known compounds or may be prepared by methods known in the literature or processes known to those skilled in the art.

Compounds of formula (II) may be prepared from compounds of formula (IV) by removal of the protecting group $P^1$, e.g. t-butyloxycarbonyl (Boc), under standard conditions. For example, where $P^1$ represents Boc, removal of the protecting group may be effected under acidic conditions, using for example hydrogen chloride in a solvent such as dioxan or methanol, or trifluoroacetic acid (TFA) in a solvent such as dichloromethane (DCM).

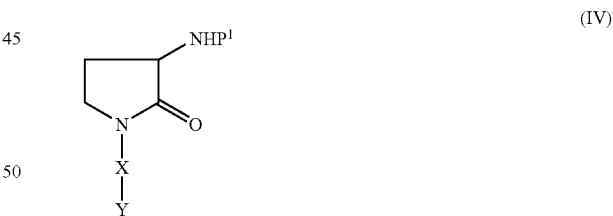

Compounds of formula (IV) may be prepared from compounds of formula (V):

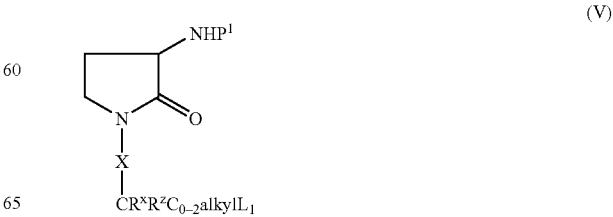

where $L_1$ is a suitable leaving group such as halide, e.g. bromide, by reaction with $HNR^cR^d$, which can be used in excess, optionally in the presence of sodium iodide, in a suitable solvent, e.g. tetrahydrofuran (THF) or ethylene glycol dimethylether, suitably at room temperature to 60° C.

Compounds of formula $HNR^cR^d$ are known compounds or may be prepared by methods known in the literature or processes known to those skilled in the art.

Compounds of formula (V) may be prepared from compounds of formula (VI):

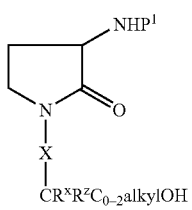

(VI)

by halogenation methods well known to persons skilled in the art. For example, when $L_1$ is bromide, bromination may be effected with carbon tetrabromide, in a suitable solvent, e.g. DCM, in the presence of a phosphine, e.g. triphenylphosphine, suitably at 0° C. to room temperature.

Compounds of formula (VI), where $CR^xR^zC_{0-2}alkylOH$ represents $CR^xHOH$, may be prepared from compounds of formula (VII):

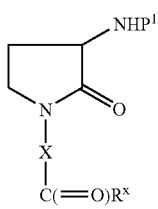

(VII)

by reduction under standard conditions, e.g. by treatment with a nucleophilic hydride source, e.g. sodium borohydride, in a suitable solvent, e.g. methanol, suitably at 0° C. to room temperature.

Alternatively, compounds of formula (VI), where $CR^xR^zC_{0-2}alkylOH$ represents $CR^xHOH$, may also be prepared from compounds of formula (VIIa):

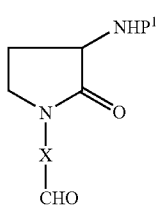

(VIIa)

by treatment with an organometallic alkyl compound, e.g. an alkyl magnesium chloride, in a suitable solvent, e.g. THF, suitably at 0° C. to room temperature, e.g. 0–10° C.

Compounds of formula (VII) may be prepared from compounds of formula (VIII):

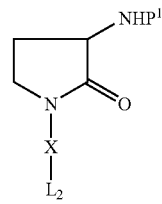

(VIII)

where $L_2$ is a suitable leaving group such as halide, e.g. iodide, by reaction with a suitable vinyl ether, e.g. n-butyl vinyl ether, in the presence of a base, e.g. sodium carbonate, in a suitable solvent, e.g. N,N-dimethylformamide (DMF), in the presence of a metal catalyst, e.g. palladium(II) acetate, and a suitable ligand, e.g. 1,3-bis(diphenylphosphino)propane, suitably at elevated temperature (e.g. 60–110° C.) and suitably under an inert atmosphere, e.g. nitrogen; followed by hydrolysis with an appropriate aqueous acid, e.g. aqueous formic acid, in a suitable solvent, e.g. MeCN, suitably at room temperature.

Compounds of formula (VIIa) may be prepared from compounds of formula (VIII) where $L_2$ is a suitable leaving group such as halide, e.g. iodide, by reaction with carbon monoxide gas, in the presence of a base, e.g. triethylamine, optionally in the presence of a suitable reductant e.g. triethylsilane, in a suitable solvent, e.g. DMF, in the presence of a metal catalyst, e.g. palladium(II) acetate, and a suitable ligand, e.g. 1,1'-bis(diphenylphosphino) ferrocene, suitably at elevated temperature (e.g. 60–110° C.).

Vinyl ethers are known compounds or may be prepared by methods known in the literature or processes known to those skilled in the art.

Compounds of formula (VIII) may be prepared from compounds of formula (IX):

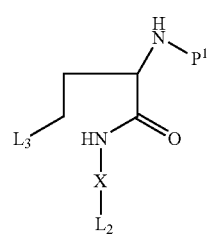

(IX)

by cyclisation where $L_3$ represents a suitable leaving group, e.g. hydroxyl. For example, when $L_3$ is a hydroxyl group, the ring closure may be performed by treatment with a mixture of (i) aryl or alkyl phosphine, e.g. tri-n-butylphosphine, and (ii) a suitable azodicarboxylate derivative, e.g. 1,1'-(azodicarbonyl)-dipiperidine, in a suitable solvent, e.g. THF, suitably at 0° C. to room temperature.

It will be appreciated by persons skilled in the art that compounds of formula (IX) may be prepared by interconversion, utilising other compounds of formula (IX) which are optionally protected by standard protecting groups, as precursors. For instance, compounds of formula (IX) where $L_3$ is OH, may be converted into compounds of formula (IX) possessing alternative substituents at $L_3$, e.g. halogen, $S^+MeR$ $W^-$ or $OSO_2R$, by methods well known in the art (see for example Smith, M. B. and March, J., Advanced Organic Chemistry, 5$^{th}$ Edition 2001, John Wiley & Sons). Generally, R will represent alkyl or aralkyl and W will represent sulphate or halide, e.g. iodide. In such cases the ring closure may be performed by treatment with a base in a suitable solvent, e.g. MeCN.

Compounds of formula (IX), where $L_3$ is a hydroxyl group, may be prepared by reacting compounds of formula (X) with compounds of formula (XI):

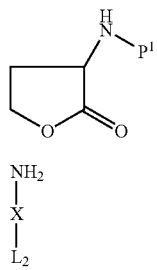

(X)

(XI)

wherein $P^1$ is a suitable protecting group as described above. The reaction is conveniently carried out by addition of a suitable activating agent, e.g. trimethylaluminium, to compounds of formula (XI) in a suitable solvent, e.g. DCM, under an inert atmosphere, e.g. nitrogen, suitably at room temperature followed by addition of a compound of formula (X) in a compatible solvent, e.g. DCM.

Compounds of formula (XI) are known compounds or may be prepared by methods known in the literature or processes known to those skilled in the art.

Compounds of formula (X) are known in the art or may be prepared from compounds of formula (XII) where HA is a suitable acid, e.g. hydrochloric acid, using methods well known to those skilled in the art. See, for example, "Protective groups in organic synthesis" by T. W. Greene and P.G.M. Wuts (John Wiley & sons 1991) or "Protecting Groups" by P. J. Kocienski (Georg Thieme Verlag 1994).

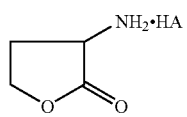

(XII)

Compounds of formula (XII) are known compounds or may be prepared by methods known in the-literature or processes known to those skilled in the art.

There is provided a further process (B) for preparing compounds of formula (I). According to process (B), compounds of formula (I) may be prepared from compounds of formula (XIII):

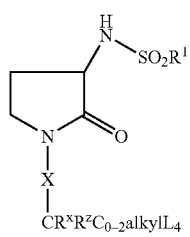

(XIII)

where $L_4$ is a suitable leaving group, such as halide, e.g. bromide, by reaction with $HNR^cR^d$, which can be used in excess, in a suitable solvent, e.g. THF, suitably at room temperature to 60° C.

Alternatively, compounds of formula (I) where $R^c$ and $R^d$ independently represent hydrogen may be prepared from compounds of formula (XIII) by reaction with sodium diformamide in a suitable solvent, e.g. DMF, suitably at elevated temperature, e.g. 40–60° C., followed by hydrolysis with an appropriate aqueous acid, e.g. hydrochloric acid (HCl), suitably at elevated temperature, e.g. 40–60° C.

Compounds of formula (XIII) may be prepared from compounds of formula (XIV):

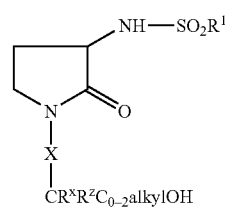

(XIV)

by halogenation methods well known to persons skilled in the art. For example, when $L_4$ is bromide, bromination may be effected with carbon tetrabromide, in a suitable solvent, e.g. DCM, in the presence of a phosphine, e.g. triphenylphosphine, suitably at 0° C. to room temperature.

Compounds of formula (XIV), where $CR^xR^zC_{0-2}$alkylOH represents $CR^xHOH$, may be prepared from compounds of formula (XV):

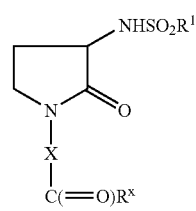

(XV)

by reduction under standard conditions, e.g. by treatment with a nucleophilic hydride source, e.g. sodium borohydride, in a suitable solvent, e.g. methanol, suitably at 0° C. to room temperature.

Compounds of formula (XV) may be prepared by reaction of compounds of formula (XVI) where HA is a suitable acid, e.g. hydrochloric acid:

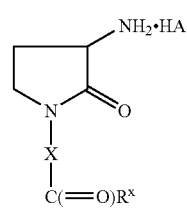

(XVI)

with compounds of formula (III), where V is a suitable leaving group, such as a halide, e.g. chloride. The reaction is conveniently carried out in the presence of a base, e.g. DIPEA, and in a suitable solvent, e.g. MeCN, suitably at room temperature.

Compounds of formula (XVI) may be prepared from compounds of formula (VII) by removal of the protecting group $P^1$, e.g. Boc, under standard conditions. For example, where $P^1$ represents Boc, removal of the protecting group may be effected under acidic conditions, using for example hydrogen chloride in a solvent such as dioxan.

There is provided a further process (C) for preparing compounds of formula (I) where $R^2$ is a substituent other than hydrogen, which comprises reacting compounds of formula (I) where $R^2$ is hydrogen with compounds of formula (XVII):

$$R^2\text{—T} \quad \text{(XVII)}$$

wherein $R^2$ is —$C_{1-6}$alkyl, —$C_{1-3}$alkylCONR$^a$R$^b$, —$C_{1-3}$alkylCO$_2$C$_{1-4}$alkyl or —CO$_2$C$_{1-4}$alkyl and T is a suitable leaving group such as that derived from a hydroxyl group or halide, e.g. bromide, optionally followed by removal of the alkyl protecting group, e.g. t-Butyl, under standard conditions to form a compound wherein $R^2$ is $C_{1-3}$alkylCO$_2$H. When T is halide, the reaction is effected in a suitable organic solvent, e.g. THF or DMF, in the presence of a base, e.g. lithium hexamethyldisilazide (LiHMDS), potassium carbonate or sodium carbonate at a temperature range from $-78°$ C. to $+50°$ C., suitably $-78°$ C. to room temperature. Furthermore, it will appreciated that the substituent $R^2$, other than hydrogen, may be introduced at various intermediate stages by methods well known to those skilled in the art. When T is a hydroxyl group, the reaction is effected under Mitsunobu conditions (for examples see Hughes, David L. Progress in the Mitsunobu reaction. A review. Organic Preparations and Procedures International (1996), 28(2), 127–64.). For example, the reaction may be performed by treatment of compounds of formula (I) where $R^2$ represents H with an aryl or alkyl phosphine, e.g. triphenylphosphine, optionally bound to polymer-support, and an azodicarboxylate derivative, e.g. di-tert-butyl azodicarboxylate, in a suitable solvent, e.g. THF, followed by addition of compounds of formula (XVII) where T represents OH, optionally in a suitable solvent, e.g. THF, suitably at room temperature.

When X-Y contains a group reactive to compounds of formula (XVII), such groups may be protected prior to the reaction using methods well known in the art and such protecting groups removed under standard conditions to provide compounds of formula (I) where $R^2$ is a substituent other than hydrogen after completion of the reaction of compounds of formula (I) where $R^2$ is hydrogen with compounds of formula (XVII).

Compounds of formula (XVII) are known compounds or may be prepared by methods known in the literature or processes known to those skilled in the art.

Furthermore, it will appreciated that the substituent $R^2$, other than hydrogen, may be introduced at various intermediate stages by methods well known to those skilled in the art.

Compounds of formula (I) where $R^c$ and/or $R^d$ are hydrogen may be converted to other compounds of formula (I) by processes known to those skilled in the art, for example, where $R^c$ and/or $R^d$ are converted to $C_{1-4}$alkyl by reductive alkylation. For example, the reaction is conveniently carried out using a suitable aldehyde, in the presence of a reducing agent, e.g. sodium triacetoxyborohydride or sodium cyanoborohydride, in a suitable solvent, e.g. MeCN, suitably at room temperature.

There is provided a further process (D) for preparing compounds of formula (IV) where Y represents CHR$^x$N R$^c$R$^d$. According to process (D), compounds of formula (I) where R$^z$ is not hydrogen may be prepared from compounds of formula (VII) by reaction with an amine HNR$^c$R$^d$ in a suitable solvent, e.g. DCM, to form an intermediate imine or iminium species which is then reacted with a suitable organometallic agent, e.g. a Grignard reagent, in a suitable solvent, e.g. THF, suitably at $0°$ C. to room temperature.

According to a further process (E) compounds of formula (VI) where $C_{0-2}$alkyl represents $C_{1-2}$alkyl may be prepared from compounds of formula (XVIII)

where $P^3$ is a suitable hydroxyl protecting group, by removal of the protecting group under standard conditions using methods well known to those skilled in the art. See, for example, "Protective groups in organic synthesis" by T. W. Greene and P. G. M. Wuts (John Wiley & sons 1991) or "Protecting Groups" by P. J. Kocienski (Georg Thieme Verlag 1994).

Compounds of formula (XVIII) may be prepared from compounds of formula (XIX):

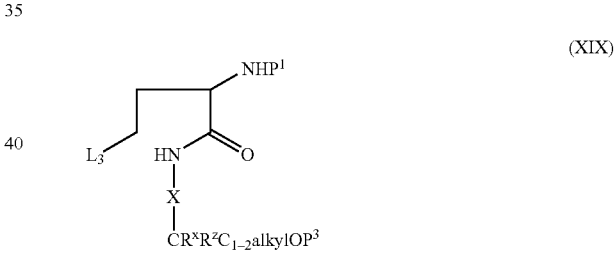

by cyclisation where $L_3$ represents a suitable leaving group. For example, when $L_3$ is a hydroxyl group, the ring closure may be performed by treatment with a mixture of (i) aryl or alkyl phosphine, e.g. tri-n-butylphosphine, and (ii) a suitable azodicarboxylate derivative, e.g. 1,1'-(azodicarbonyl)-dipiperidine, in a suitable solvent, e.g. THF, suitably at $0°$ C. to room temperature.

It will be appreciated by persons skilled in the art that compounds of formula (XIX) may be prepared by interconversion, utilising other compounds of formula (XIX) which are optionally protected by standard protecting groups, as precursors. For instance, compounds of formula (XIX) where $L_3$ is OH, may be converted into compounds of formula (XIX) possessing alternative substituents at $L_3$, e.g. halogen, S$^+$MeR W$^-$ or OSO$_2$R, by methods well known in the art (see for example Smith, M. B. and March, J., Advanced Organic Chemistry, 5$^{th}$ Edition 2001, John Wiley & Sons). Generally R will represent alkyl or aralkyl and W will represent sulphate or halide, especially iodide. In such cases the ring closure may be performed by treatment with a base in a suitable solvent, e.g. MeCN.

Compounds of formula (XIX), where $L_3$ is a hydroxyl group, may be prepared by reacting compounds of formula (XX) with compounds of formula (X):

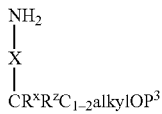
(XX)

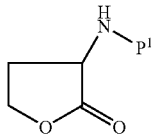
(X)

wherein $P^1$ is a suitable protecting group as described above. The reaction is conveniently carried out by addition of a suitable activating agent, e.g. trimethylaluminium, to compounds of formula (XX) in a suitable solvent, e.g. DCM, under an inert atmosphere, e.g. nitrogen, suitably at room temperature followed by addition of compounds of formula (X) in a compatible solvent, e.g. DCM.

Compounds of formula (XX) may be prepared by methods known in the art, e.g. from compounds of formula (XXI):

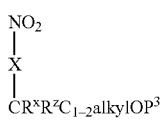
(XXI)

by hydrogenation in the presence of a suitable catalyst, e.g. 10% palladium on carbon, in a suitable solvent such as ethanol, suitably at atmospheric pressure and room temperature.

Compounds of formula (XXI), where $P^3$ is a suitable protecting group, may be prepared from compounds of formula (XXII):

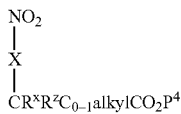
(XXII)

where $P^4$ represents hydrogen or an alkyl or aralkyl group by reduction processes well-known to those skilled in the art. For example, when $P^4$ represents a hydrogen, compounds of formula (XXI) may be prepared by reduction with a hydride source, e.g., diborane, in a suitable solvent, e.g. THF, suitably at 0° C. to room temperature followed by protection with a suitable $P^3$ protecting group using methodologies well known to those skilled in the art. See, for example, "Protective groups in organic synthesis" by T. W. Greene and P. G. M. Wuts (John Wiley & sons 1991) or "Protecting Groups" by P. J. Kocienski (Georg Thieme Verlag 1994).

Compounds of formula (XXII), where $C_{0-1}$alkyl represents $C_1$alkyl, may be prepared from compounds of formula (XXIII), where $P^4$ is a hydrogen, by chain extension processes well-known to those skilled in the art.

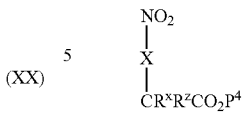
(XXIII)

For example, compounds of formula (XXII) where $C_{0-1}$alkyl represents $C_1$alkyl, and $P^4$ is a hydrogen, may be prepared from compounds of formula (XXIII), where $P^4$ is a hydrogen, via the Arndt-Eistert synthesis. For example, compounds of formula (XXII) where $C_{0-1}$alkyl represents $C_1$alkyl, and $P^4$ is a hydrogen, may be prepared from compounds of formula (XXIII), where $P^4$ is a hydrogen, by activation to an acid halide, e.g., acid chloride, using standard methodologies, followed by reaction with diazomethane in a suitable solvent, e.g. diethyl ether, suitably at 0° C. to room temperature, followed by Wolff rearrangement with a silver salt, e.g. silver oxide, and water, optionally in the presence of a base, e.g. triethylamine, in a suitable solvent.

Compound of formula (XXIII), where $P^4$ is a suitable carboxylic acid protecting group, may be prepared from compounds of formula (XXIV):

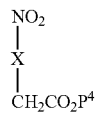
(XXIV)

by alkylation chemistries well known in the art (see for example Smith, M. B. and March, J., Advanced Organic Chemistry, 5th Edition 2001, John Wiley & Sons).

Compounds of formula (XXIV) are known compounds or may be prepared by methods known in the literature or processes known to those skilled in the art.

There is provided a further process (F) for preparing compounds of formula (I) where X represents phenyl, Y represents —CH($R^x$)$NR^cR^d$ and $R^c$ and $R^d$ each represent the same $C_{1-6}$alkyl substituent. According to process (F), a compound of formula (I) may be prepared by reacting a compound of formula (XXV) where $R^0$ represents 0–2 optional substituents on the phenyl ring selected from: halogen, —$C_{1-4}$alkyl, —$C_{2-4}$alkenyl, —$CN_1$, —$CF_3$, —$NR^aR^b$, —$C_{0-4}$alkyl$OR^e$, —C(O)$R^f$ and C(O)$NR^aR^b$ and/or an acid addition salt thereof:

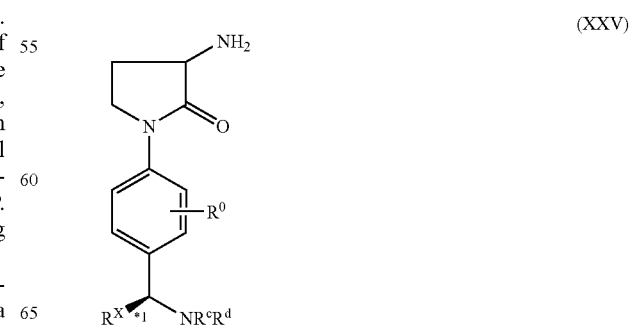
(XXV)

with a compound of formula (III) where V is a suitable leaving group, such as a halide, for example chloride. The reaction is conveniently carried out in the presence of a base, e.g. DIPEA, and in a suitable solvent, e.g. MeCN, suitably at 0° C. to room temperature.

A compound of formula (XXV) may be prepared from a compound of formula (XXVI) by removal of the protecting group $P^1$, e.g. Boc, under standard conditions. For example, where $P^1$ represents Boc, removal of the protecting group may be effected under acidic conditions using for example, hydrogen chloride in a solvent such as dioxan.

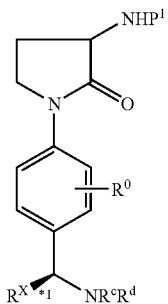

(XXVI)

A compound of formula (XXVI) may be prepared from compounds of formula (XXVII):

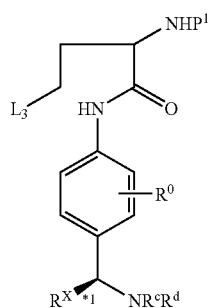

(XXVII)

wherein $P^1$ is a suitable protecting group as described above, by cyclisation where $L_3$ represents a suitable leaving group, e.g. hydroxyl. For example, when $L_3$ is a hydroxyl group, the ring closure may be performed by treatment with a mixture of (i) aryl or alkyl phosphine, e.g. tri-n-butylphosphine, and (ii) a suitable azodicarboxylate derivative, e.g. 1,1'-(azodi-carbonyl)-dipiperidine, in a suitable solvent, e.g. THF, suitably at 0° C. to room temperature.

A compound of formula (XXVII), where $L_3$ is a hydroxyl group may be prepared by reacting a compound of formula (XXVIII) with a compound of formula (X):

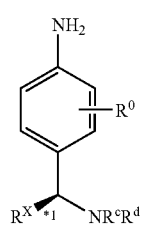

(XXVIII)

The reaction is conveniently carried out by addition of a suitable activating agent, e.g. trimethylaluminium, to a compound of formula (XXVIII) in a suitable solvent, e.g. DCM, under an inert atmosphere, e.g. nitrogen, suitably at room temperature to 40° C., followed by addition of a compound of formula (X) in a compatible solvent, e.g. DCM.

A compound of formula (XXVIII) may be prepared from a compound of formula (XXIX):

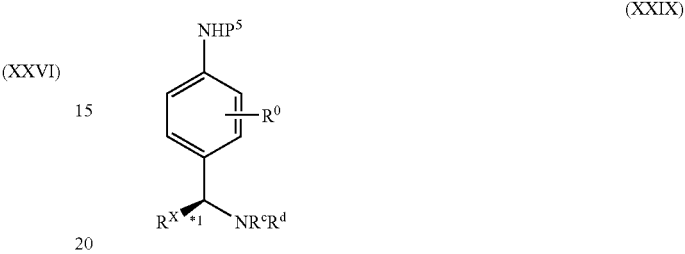

(XXIX)

where $P^5$ represents a suitable protecting group where appropriate, by removal of the protecting group $P^5$ e.g. Boc, where present, under standard conditions. For example, where $P^5$ represents Boc, removal of the protecting group may be effected under acidic conditions, using for example, hydrogen chloride in a solvent such as dioxan.

A compound of formula (XXIX) may be prepared by reaction of a compound of formula (XXX):

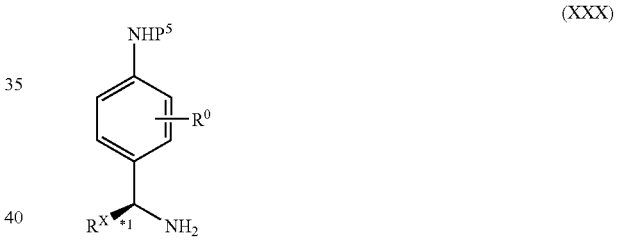

(XXX)

with a compound of formula (XXXI):

(XXXI)

where $P^5$ represents a protecting group or hydrogen where appropriate, by reductive alkylation. For example, where $R^c$ and $R^d$ each represents methyl the reaction is suitably carried out in the presence of an acid, e.g. $HCO_2H$ and formaldehyde, suitably at elevated temperature, e.g. 50–70° C. Where $R^c$ and $R^d$ each represent $C_{2-6}$ alkyl the reaction is conveniently carried out in the presence of a reducing agent, e.g. sodium triacetoxyborohydride or sodium cyanoborohydride, in a suitable solvent, e.g. MeCN, suitably at room temperature.

Compounds of formula (XXXI) are known compounds or may be prepared by methods known in the literature or processes known to those skilled in the art.

Compounds of formula (XXX) may be prepared from compounds of formula (XXXII):

(XXXII)

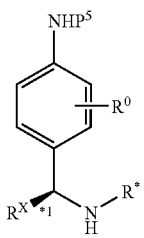

where R* represents a chiral auxiliary, for example (R)-1-phenylethyl or (S)-1-phenylethyl, by transfer hydrogenation in the presence of a suitable catalyst, e.g. Pd(C), and ammonium formate, in a suitable solvent, e.g. methanol or ethanol, suitably at elevated temperature, e.g. 50–70° C. Alternatively, compounds of formula (XXX) may be prepared from a compounds of formula (XXXII), where R* represents a chiral auxiliary, for example (R)-1-phenylethyl or (S)-1-phenylethyl, by catalytic hydrogenation in the presence of a suitable catalyst, e.g. Pd(C), in a suitable solvent, e.g. ethyl acetate, suitably at elevated temperature, e.g. 50–70° C., suitably at elevated pressure, e.g. 2–4 atm.

Where the chiral auxiliary is (R)-1-phenylethyl or (S)-1-phenylethyl, a compound of formula (XXXII) may be prepared by reacting a compound of formula (XXXIII) with a compound of formula (XXXIV):

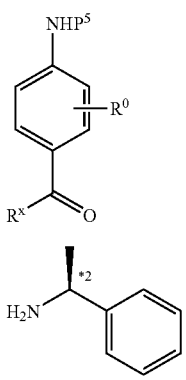

in the presence of a Lewis acid and dehydrating agent, e.g. titanium tetrachloride (TiCl$_4$), and a suitable solvent, e.g. toluene, followed by reduction under standard conditions, e.g. by treatment with a nucleophilic hydride source, e.g. sodium borohydride, in a suitable solvent, e.g. methanol, suitably at 0° C. to room temperature.

Compounds of formula (XXXIII) are known compounds or may be prepared by methods known in the literature or processes known to those skilled in the art.

Compounds of formula (XXXIV) are commercially available or may be prepared by processes known to those skilled in the art.

It will be understood by persons skilled in the art that use of the alternative diastereoisomer at (*2) in a compound of formula (XXXIV) will result in a compound of formula (I) of the alternative stereochemistry at (*1).

There is provided a further process (G) for preparing compounds of formula (I) where Y represents —C(R$^x$)(R$^z$)NR$^c$R$^d$ and R$^x$ and R$^z$ both represent C$_{1-4}$alkyl and R$^2$ represents hydrogen. According to process (G) compounds of formula (I) may be prepared from compounds of formula (XXXV):

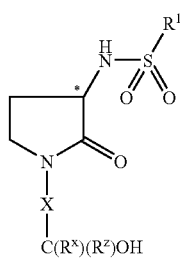

(XXXV)

by treatment with hydrogen chloride in the presence of zinc chloride, in a suitable solvent, e.g. DCM, suitably at 0–10° C., followed by reaction with HNR$^c$R$^d$, e.g. dimethylamine, in a suitable solvent, e.g. THF, suitably at elevated temperature, e.g. 60–80° C.

Compounds of formula (XXXV) may be prepared from compounds of formula (XXXVI):

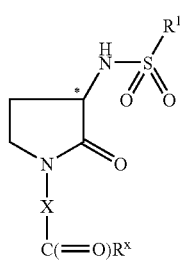

(XXXVI)

by treatment with a Lewis Acid, e.g. TiCl$_4$, and a nucleophillic alkyl source, e.g. dimethyl zinc, in a suitable solvent, e.g. diethyl ether, suitably below room temperature, e.g. −30° C. to −78° C., or by treatment with an organometallic alkyl compound, e.g. an alkyl magnesium chloride, in a suitable solvent, e.g. THF, suitably at 0° C. to room temperature, e.g. 0–10° C.

Compounds of formula (XXXVI) may be prepared from compounds of formula (XXXVII):

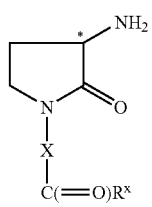

(XXXVII)

by reacting compounds of formula (XXXVI) with compounds of formula (III) where V is a suitable leaving group, such as a halide, e.g. chloride. The reaction is conveniently carried out in the presence of a base, e.g. pyridine, and in a suitable solvent, e.g. MeCN, suitably at 0° C. to room temperature.

Compounds of formula (XXXVII) may be prepared from compounds of formula (VII) by removal of the protecting group $P^1$, e.g. Boc, under standard conditions. For example, where $P^1$ represents Boc, removal of the protecting group may be effected under acidic conditions, using for example hydrogen chloride in a solvent such as dioxan.

There is provided a further process (H) for preparing compounds of formula (I) where Y represents —C(R$^x$)NR$^c$R$^d$, R$^x$ represents $C_{1-4}$alkyl and R$^c$ and R$^d$ independently represent hydrogen, $C_{1-6}$alkyl, or together with the N atom to which they are bonded form a 4-, 5-, 6- or 7-membered non-aromatic heterocyclic ring. According to process (H), compounds of formula (I) may be prepared from compounds of formula (XXXVIIII):

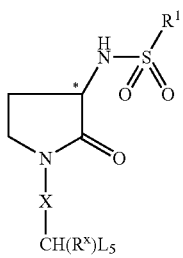

(XXXVIII)

where $L_5$ is a suitable leaving group such as halide, e.g. bromide, by reaction with HNR$^c$R$^d$, which can be used in excess, in a suitable solvent, e.g. THF, suitably at −10 to +10° C.

Compounds of formula HNR$^c$R$^d$ are known compounds or may be prepared by methods known in the literature or processes known to those skilled in the art.

Compounds of formula (XXXVIII) may be prepared from compounds of formula (XXXIX):

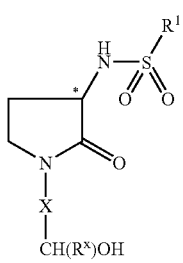

(XXXIX)

by halogenation methods well known to persons skilled in the art. For example, when $L_5$ is bromide, bromination may be effected with N-bromosuccinimide (NBS), in a suitable solvent, e.g. DCM, in the presence of a phosphine e.g. triphenyl phosphine, suitably at −10 to +10° C.

Compounds of formula (XXXIX) may be prepared from compounds of formula (XL):

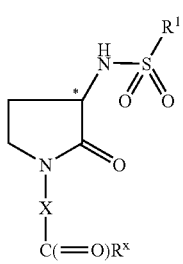

(XL)

by reduction under standard conditions, e.g. by treatment with a nucleophilic hydride source e.g. sodium borohydride, in a suitable solvent, e.g. methanol, suitably at 0° C. to room temperature.

Compounds of formula (XL) may be prepared by reaction of compounds of formula (XLI):

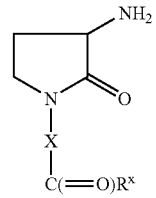

(XLI)

with a compound of formula (III) where V is a suitable leaving group, such as a halide, for example chloride. The reaction is conveniently carried out in the presence of a base, e.g. pyridine, and in a suitable solvent, e.g. MeCN, suitably at 0° C. to room temperature.

Compounds of formula (XLI) may be prepared by reaction of compounds of formula (XLII)

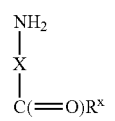

(XLII)

with compounds of formula (XLIII):

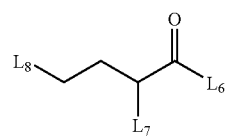

(XLIII)

where $L_6$ is a suitable leaving group, e.g. chloride, and $L_7$ and $L_8$ are suitable leaving groups, e.g. bromide, in a suitable solvent, e.g. MeCN, in the presence of a base, e.g. $K_2CO_3$, suitably at −10 to +10° C., followed by reaction with aqueous ammonia suitably at room temperature to 40° C.

Compounds of formula (XLII) and (XLIII) are known compounds or may be prepared by methods known in the literature or processes known to those skilled in the art.

It will be appreciated by those skilled in the art that compounds of formula (I) or a solvate thereof may be synthesized from appropriate intermediates via solid phase chemistry processes.

Those skilled in the art will appreciate that in the preparation of compounds of formula (I) and/or solvates thereof it may be necessary and/or desirable to protect one or more sensitive groups in the molecule or the appropriate intermediate to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J.

Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl or aralkyl type protecting groups (e.g. benzyl, trityl, chlorotrityl). Examples of suitable hydroxyl protecting groups may include for example alkyl silyl groups, such as trimethylsilyl or tert-butyldimethylsilyl; alkyl ethers such as tetrahydropyranyl or tert-butyl; or esters such as acetate. Examples of carboxylic acid protecting groups may include for example aralkyl groups, e.g. benzyl, or alkyl groups, e.g. t-butyl.

Various intermediate compounds used in the above-mentioned process, including but not limited to certain compounds of formulae (II), (IV), (V), (VI), (VII), (VIIa), (VIII), (IX), (XIII), (XIV), (XV), (XVI), (XVIII), (XIX), (XX), (XXI), (XXII), (XXIII), (XXV), (XXVI), (XXVII), (XXVIII), (XXIX), (XXX), (XXXII), (XXXV), (XXXVI) and (XXXVII) constitute a further aspect of the present invention.

The present invention will now be further illustrated by the accompanying examples which should not be construed as limiting the scope of the invention in any way.

All publications, including but not limited to patents and patent applications, cited in this specification are herein incorporated by reference as if each individual publication were specifically and individually indicated to be incorporated by reference herein as though fully set forth.

EXAMPLES

| Abbreviations | |
|---|---|
| THF | Tetrahydrofuran |
| MeCN | Acetonitrile |
| DCM | Dichloromethane |
| DMF | N,N-dimethylformamide |
| DIPEA | N,N-diisopropylethylamine |
| Boc | t-butyloxycarbonyl |
| b | broad |
| d | doublet |
| dd | doublet of doublets |
| m | multiplet |
| q | quartet |
| s | singlet |
| t | triplet |
| min | minutes |
| h | hours |

Intermediate 1

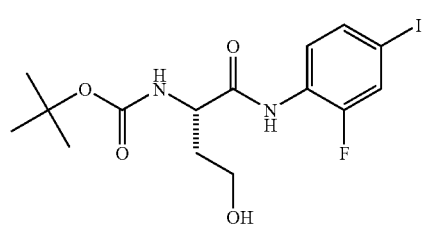

1,1-Dimethylethyl((1S)-1-{[(2-fluoro-4-iodophenyl)amino]carbonyl}-3-hydroxypropyl)-carbamate A solution of 2-fluoro-4-iodoaniline (7.11 g) in anhydrous DCM (40 ml) under nitrogen at 0° C. was treated dropwise with trimethylaluminium (2N in heptane; 15 ml). The mixture was allowed to stir for 30 min before a solution of 1,1-dimethylethyl [(3S)-2-oxotetrahydro-3-furanyl]carbamate (5.03 g), in anhydrous DCM (35 ml), was added dropwise. The reaction was allowed to warm up to ambient temperature and stirred for 18 h, before quenching with 10% aqueous citric acid (10 ml). Saturated aqueous potassium sodium tartrate (100 ml) was then added with stirring followed by separation of the organic and aqueous layers. The organic layer was dried (over magnesium sulphate) and concentrated under reduced pressure. The residue was purified using Biotage™ chromatography (silica, eluting with cyclohexane:ethyl acetate 3:2) to afford an off-white solid which was an inseparable mixture (c. 1:2) of the starting material and the title compound (5.55 g).

Mass spectrum: Found: MH+ 439

Intermediate 2

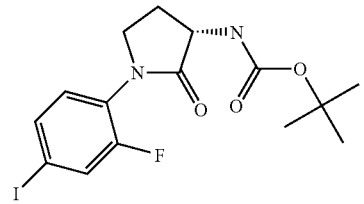

1,1-Dimethylethyl[(3S)-1-(2-fluoro-4-iodophenyl)-2-oxo-3-pyrrolidinyl]carbamate

To a solution of crude Intermediate 1 (5.55 g) and tri-n-butylphosphine (3.49 ml) in anhydrous THF (100 ml) under nitrogen at 0° C. was added solid 1,1'-(azodicarbonyl)-dipiperidine (3.53 g). The solution was allowed to warm to ambient temperature and stirred for 18 h. The mixture was then diluted with cyclohexane (100 ml) and the precipitate filtered off. The filtrate was then concentrated under reduced pressure and the residue purified using Biotage™ chromatography (silica, eluting with cyclohexane:ethyl acetate 2:1) to give the title compound (2.93 g) as a white solid.

Mass spectrum: Found: MH+ 421

Intermediate 3

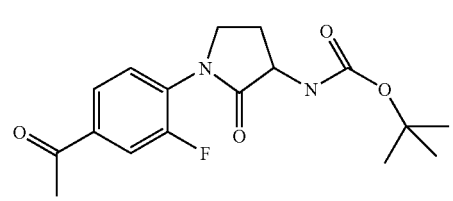

1,1-Dimethylethyl[1-(4-acetyl-2-fluorophenyl)-2-oxo-3-pyrrolidinyl]carbamate

A degassed solution of Intermediate 2 (1.05 g) in dry DMF (20 ml) was treated sequentially with sodium carbonate (0.42 g), triethylamine (0.67 ml), n-butyl vinyl ether (1.62 ml), 1,3-bis(diphenylphosphino)propane (0.124 g) and palladium(II) acetate (0.034 g). The mixture was heated to 80° C. under nitrogen for 7 h, allowing to cool and stirred overnight. Solvent was removed under reduced pressure and the crude residue treated with 0.1% formic acid: water (10 ml) and MeCN (10 ml). The mixture was stirred at ambient temperature for 4 h before concentrating under reduced pressure. The residue was dissolved in minimum DCM and purified using pre-conditioned silica SPE (20 g/60 cc) eluting with cyclohexane:ethyl acetate (5:1 to neat ethyl acetate) to give the title compound (0.362 g) as a yellow powder.

Mass spectrum: Found: MH+ 337

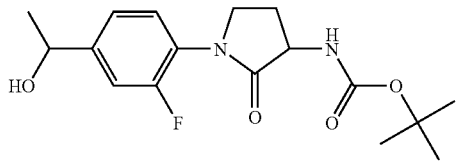

Intermediate 4

1,1-Dimethylethyl{1-[2-fluoro-4-(1-hydroxyethyl) phenyl]-2-oxo-3-pyrrolidinyl}carbamate Intermediate 3 (110 mg) in dry methanol (4 ml) was treated with sodium borohydride (0.012 g) and the mixture stirred at ambient temperature for 18 h under nitrogen. The reaction was quenched with 3 drops of water and concentrated under reduced pressure, partitioning the residue between DCM and water. The separated organic layer was passed through a hydrophobic frit and concentrated under reduced pressure to give the title compound (0.103 g) as a cream solid.

Mass spectrum: Found: MH+ 339
H.p.l.c. R$_t$ 2.61 min

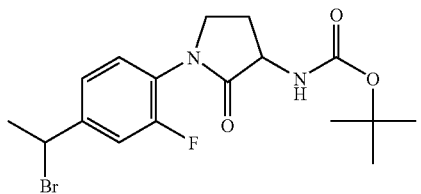

Intermediate 5

1,1-Dimethylethyl{1-[4-(1-bromoethyl)-2-fluorophenyl]-2-oxo-3-pyrrolidinyl}carbamate Intermediate 4 (0.103 g) in dry DCM (6 ml) at 0° C. was treated with carbon tetrabromide (0.119 g) and stirred for 3 min. To the mixture was added triphenylphosphine (0.094 g) in portions and the reaction stirred at 0° C. for 1.5 h before more carbon tetrabromide (0.119 g) and triphenylphosphine (0.094 g) were added. The reaction was warmed up to ambient temperature and stirred overnight under nitrogen. The mixture was diluted with DCM and washed with water. The separated organic layer was passed through a hydrophobic frit and concentrated under reduced pressure, to a small volume, and purified using pre-conditioned silica SPE (5 g/20 cc) eluting with cyclohexane: ethyl acetate (4:1 to 2:1) to give the title compound (0.026 g) as a cream solid.

Mass spectrum: Found: MH+ 403

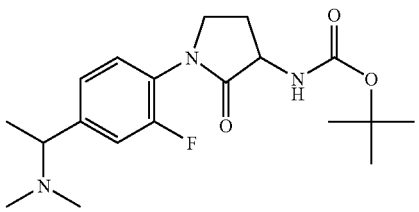

Intermediate 6

1,1-Dimethylethyl(1-{4-[1-(dimethylamino)ethyl]-2-fluorophenyl}-2-oxo-3-pyrrolidinyl)carbamate Intermediate 5 (0.027 g) was treated with 2N dimethylamine in THF (3 ml) and stirred for 18 h at ambient temperature. Solvent was removed under reduced pressure and the residue partitioned between chloroform and saturated aqueous sodium bicarbonate solution. The separated organic layer was passed through a hydrophobic frit and re-concentrated under reduced pressure. The residue was purified using SCX SPE (1 g/2 ml) eluting with DCM to 10% ammonia/methanol to give the title compound (0.019 g) as a sticky gum.

Mass spectrum: Found: MH+ 366

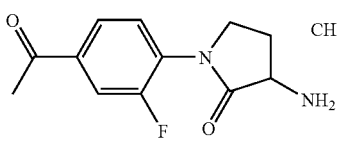

Intermediate 7

1-(4-Acetyl-2-fluorophenyl)-3-amino-2-pyrrolidinone hydrochloride

Intermediate 3 (0.156 g) was stirred in 4M hydrogen chloride/dioxan (6 ml) at ambient temperature for 2 h. The reaction was concentrated under reduced pressure to give the title compound (0.135 g) as a pale yellow solid.

Mass spectrum: Found: MH+ 237

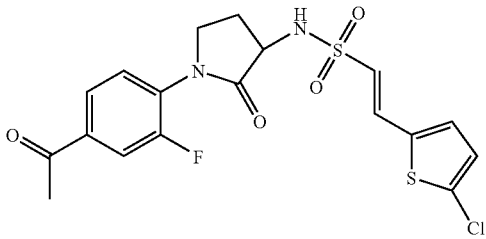

Intermediate 8

(E)-N-[1-(4-Acetyl-2-fluorophenyl)-2-oxo-3-pyrrolidinyl]-2-(5-chloro-2-thienyl)ethenesulfonamide Intermediate 7 (0.135 g) was suspended in dry MeCN (5 ml) was cooled to 0° C. and treated with DIPEA (0.19 ml), allowing to stir for 5 min. A pre-cooled solution of (E)-2-

(5-chloro-2-thienyl)ethenesulfonyl chloride (0.122 g) in dry MeCN (2 ml) was added slowly and the mixture stirred at 0° C. for 2 h before warming up to ambient temperature and stirring overnight. The mixture was concentrated under reduced pressure, partitioning the residue between DCM and saturated aqueous sodium bicarbonate. The separated organic layer was passed through a hydrophobic frit and concentrated under reduced pressure to give the title compound (0.162 g) as a pale yellow solid.

Mass spectrum: Found: (M−H)⁻ 441
H.p.l.c. $R_t$ 3.16 min

Intermediate 9

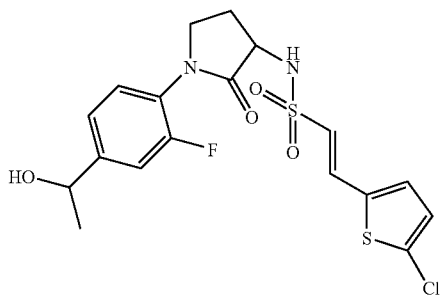

(E)-2-(5-Chloro-2-thienyl)-N-{1-[2-fluoro-4-(1-hydroxyethyl)phenyl]-2-oxo-3-pyrrolidinyl}ethenesulfonamide Intermediate 8 (0.163 g) suspended in dry methanol (5 ml) was treated with sodium borohydride (0.028 g) and the mixture stirred at ambient temperature for 90 min under nitrogen. The reaction was quenched with 3 drops of water and concentrated under reduced pressure, partitioning the residue between DCM and water. The separated organic layer was passed through a hydrophobic frit and concentrated under reduced pressure to give the title compound (0.149 g) as a beige foamy solid.

Mass spectrum: Found: MH⁺ 445
H.p.l.c. $R_t$ 3.00 min

Intermediate 10

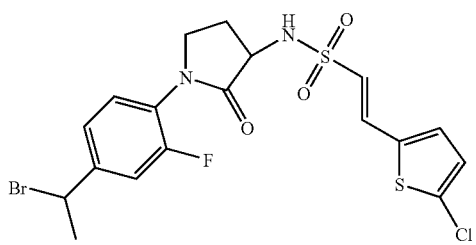

(E)-N-{1-[4-(1-Bromoethyl)-2-fluorophenyl]-2-oxo-3-pyrrolidinyl}-2-(5-chloro-2-thienyl)ethenesulfonamide A solution of Intermediate 9 (0.149 g) in dry DCM (6 ml) at 0° C. was treated with carbon tetrabromide (0.136 g) and stirred for 5 min. To the mixture was added triphenylphosphine (0.106 g) in portions and the reaction stirred at 0° C. for 2 h before more carbon tetrabromide (0.136 g) and triphenylphosphine (0.106 g) were added. The reaction was warmed up to ambient temperature and stirred overnight under nitrogen. The mixture was diluted with DCM and washed with water. The separated organic layer was passed through a hydrophobic frit and concentrated under reduced pressure, to a small volume, and purified using pre-conditioned silica SPE (5 g/20 cc) eluting with cyclohexane:ethyl acetate (10:1 to 2:1) to give the title compound (0.09 g) as a beige solid.

Mass spectrum: Found (M−H)⁻ 506

Intermediate 11

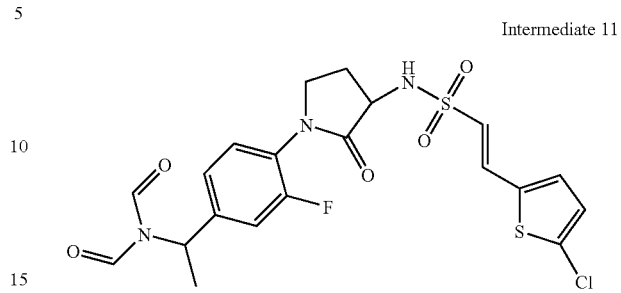

(E)-2-(5-Chloro-2-thienyl)-N-(1-{4-[1-(diformylamino)ethyl]-2-fluorophenyl}-2-oxo-3-pyrrolidinyl)ethenesulfonamide A solution of Intermediate 10 (0.09 g), in dry DMF (4 ml), was treated with sodium diformamide (0.019 g) and then heated to 50° C. under nitrogen for 3.5 h. The reaction was cooled to ambient temperature and the solvent removed under reduced pressure, partitioning the residue between DCM and water. The separated organic layer was passed through a hydrophobic frit and re-concentrated under reduced pressure to give the title compound (0.075 g) as an orange gum.

Mass spectrum: Found: MH⁻ 498

Intermediate 12

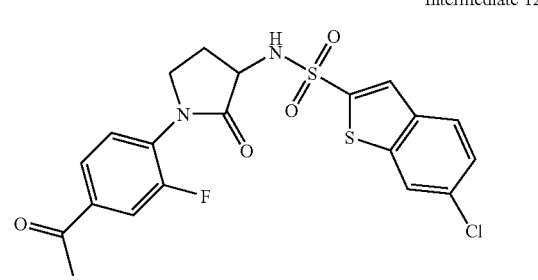

N-[1-(4-Acetyl-2-fluorophenyl)-2-oxo-3-pyrrolidinyl]-6-chloro-benzothiophene-2-sulfonamide The title compound was prepared from Intermediate 7 and 6-chloro-1-benzothiophene-2-sulphonyl chloride using the synthetic procedure described for Intermediate 8.

Mass spectrum: Found: MH⁺ 467

Intermediate 13

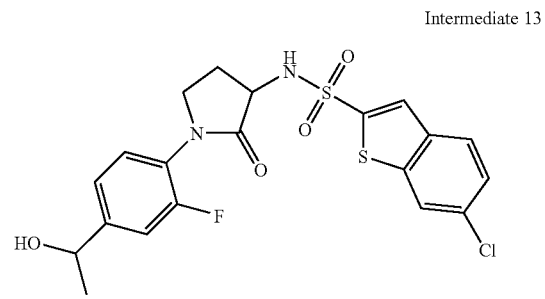

6-Chloro-N-{1-[2-fluoro-4-(1-hydroxyethyl)phenyl]-2-oxo-3-pyrrolidinyl}-1-benzothiophene-2-sulfonamide The title compound was prepared from Intermediate 12 using the synthetic procedure described for Intermediate 9.

Mass spectrum: Found: MH+ 469

Intermediate 14

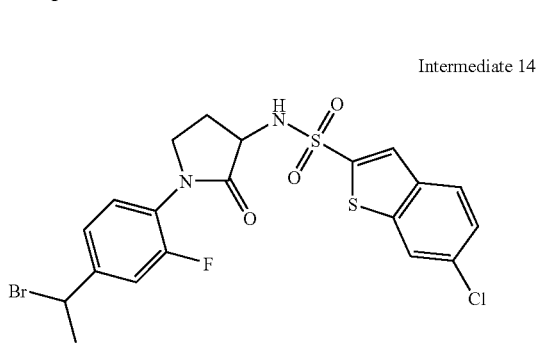

N-{1-[4-(1-Bromoethyl)-2-fluorophenyl]-2-oxo-3-pyrrolidinyl}-6-chloro-1-benzothiophene-2-sulfonamide The title compound was prepared from Intermediate 13 using the synthetic procedure described for Intermediate 10.

Mass spectrum: Found: MH+ 531

Intermediate 15

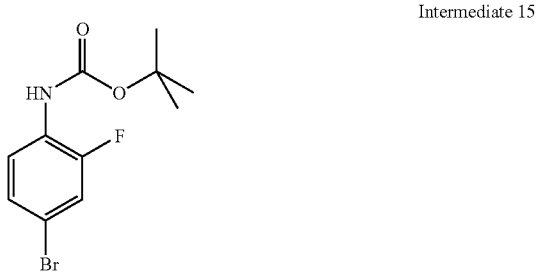

1,1-Dimethylethyl (4-bromo-2-fluorophenyl)carbamate

A solution of 4-bromo-2-fluoroaniline (40 g) in toluene (120 ml) was treated with di-tert-butyl dicarbonate (51 g) and heated at 80° C. under nitrogen for 19 h. The reaction mixture was cooled to ambient temperature and treated with a further portion of di-tert-butyl dicarbonate (10 g) and heated at 80° C. under nitrogen for 6 h. The reaction mixture was cooled to ambient temperature and concentrated under reduced pressure. The residue was purified by column chromatography on silica gel eluting with 9:1 cyclohexane: ethyl acetate. The product fractions were evaporated to dryness and the residue was partitioned between DCM (250 ml) and saturated aqueous sodium bicarbonate (200 ml). The layers were separated and the aqueous layer was washed with DCM (50 ml). The organic layers were combined, washed with saturated aqueous sodium chloride (100 ml), dried (sodium sulfate) and concentrated under reduced pressure to give the title compound (61.22 g) as a pale orange waxy solid.

$^1$H NMR (CDCl$_3$) δ: 1.54 (9H, bs), 6.67 (1H, bs, 1H), 7.2–7.3 (2H, m), 8.01 (1H, m)

Intermediate 16

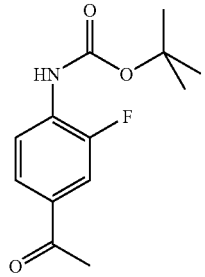

1,1-Dimethylethyl (4-acetyl-2-fluorophenyl)carbamate

A degassed solution of Intermediate 15 (30 g) in DMF (260 ml) and water (60 ml) was treated sequentially with 1,3-bis(diphenylphosphino)propane (2.82 g), palladium (II) acetate (0.696 g), anhydrous potassium carbonate (16.92 g) and butyl vinyl ether (66.9 ml). The mixture was heated to 80° C. under nitrogen for 6 h, cooled to ambient temperature and concentrated under reduced pressure. The residue was partitioned between water (300 ml) and ethyl acetate (400 ml). The layers were separated and the aqueous layer was washed with ethyl acetate (200 ml). The organic extracts were combined washed with saturated aqueous sodium chloride (300 ml), dried (over sodium sulfate) and concentrated under reduced pressure. The yellow residue was dissolved in MeCN (300 ml) and treated with water (300 m) and formic acid (5 ml). The reaction mixture was stirred at ambient temperature for 2 h and evaporated to remove the MeCN. The residue was partitioned between ethyl acetate (400 ml) and saturated aqueous sodium bicarbonate (250 ml). The layers were separated and the aqueous layer was washed with ethyl acetate (200 ml). The organic extracts were combined, washed with saturated sodium chloride (200 ml) dried (over sodium sulfate) and concentrated under reduced pressure. The residue was mixed with cyclohexane (200 ml) and solid was removed by filtration, washing with diethyl ether. The filtrate was concentrated under reduced pressure and purified on silica gel eluting with DCM to give the title compound (17.86 g) as a colourless solid.

Mass spectrum: Found: MH+ 254

Intermediate 17

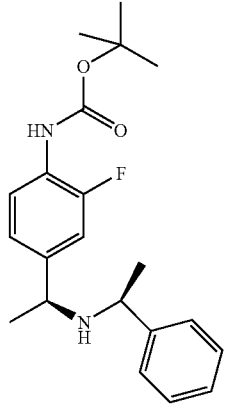

1,1-Dimethylethyl[2-fluoro-4-((1S)-1-{[(1S)-1-phenylethyl]amino}ethyl)phenyl]carbamate A solution of Intermediate 16 (3.80 g) in anhydrous toluene (60 ml) was treated sequentially with (S)-1-phenylethylamine (2.32 ml) and triethylamine (8.36 ml). A 1M solution of titanium (IV) chloride in toluene (8.25 ml) was added over 1 h and the dark suspension was stirred at ambient temperature under nitrogen for 19 h. The suspension was filtered quickly and the solid was washed with dry toluene (30 ml). The toluene solution was slowly added over 1 h and 40 min to a stirred solution of sodium borohydride (1.14 g) in dry methanol (150 ml) at −75° C. under nitrogen. The reaction mixture was stirred at −75° C. for 1 h and 20 min and was then allowed to warm to −60° C. over 30 min. Ice cold water was added to the reaction mixture over 30 min as it warmed to 0° C. 10% Aqueous ammonium chloride (10 ml) was added over 30 min and the reaction mixture was concentrated under reduced pressure and partitioned between saturated aqueous sodium bicarbonate (80 ml) and ethyl acetate (100 ml, 50 ml). The organic extracts were combined and dried (over sodium sulfate) and concentrated under reduced pressure. The residue (92:8 isomer ratio) was purified by RediSep™ silica chromatography (Combi Flash® Companion™) eluting with 10:1 cyclohexane:ethyl acetate to give the title compound (2.77 g, >99:1 isomer ratio) as a colourless oil.

Mass spectrum: Found: MH+ 359

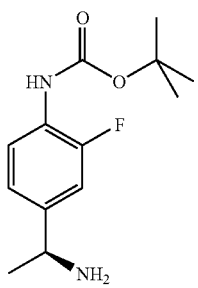

Intermediate 18

1,1-Dimethylethyl{4-[(1S)-1-aminoethyl]-2-fluorophenyl}carbamate

A mixture of Intermediate 17 (2.70 g) and 5% palladium on carbon (1 g) in ethanol (50 ml) was treated with ammonium formate (4.75 g) and stirred at ambient temperature for 5 min. The reaction mixture was then gradually heated to 65° C. over 30 min and then held at 65° C. for 1 h. The reaction mixture was cooled and filtered to remove the catalyst. The filtrate was evaporated to dryness to give the title compound (1.92 g) as a colourless solid.

$^1$H NMR (CDCl$_3$) δ: 1.38 (3H, d), 1.53 (9H, bs), 2.78 (2H, bs), 4.09 (1H, m), 6.70 (1H, bs), 7.08 (2H, m), 8.0 (1H, bm)

Intermediate 18

Method B

A solution of Intermediate 17 (92.5 g) in ethanol (800 ml) containing 10% palladium on charcoal (Degussa E101 NE/W, 50% w/w water, 9.25 g) was stirred at 55° C. under hydrogen at 50 p.s.i. for 5 h. After cooling, the catalyst was filtered and the solvent evaporated to afford 59.5 g of the title compound as a light grey solid.

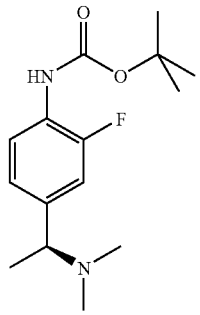

Intermediate 19

1,1-Dimethylethyl{4-[(1S)-1-(dimethylamino)ethyl]-2-fluorophenyl}carbamate

Intermediate 18 (1.92 g) was cooled in an ice bath and slowly treated with formic acid (1.46 ml) with stirring. The resulting suspension was treated with 37% aqueous formaldehyde (1.67 ml) and the reaction mixture was heated to 70° C. under nitrogen for 1 h. The yellow solution was cooled to room temperature and carefully basified with saturated aqueous sodium carbonate solution (30 ml) and extracted with ethyl acetate (3×50 ml). The organic extracts were combined, washed with saturated aqueous sodium chloride (10 ml), dried (over sodium sulfate) and evaporated to a yellow oil. Purification on a 50 g silica SPE cartridge eluting with a gradient 20:1 to 7:1 ethyl acetate:methanol gave the title compound (1.31 g) as a pale yellow oil.

Mass spectrum: Found: MH+ 283

Intermediate 19

Method B

A solution of Intermediate 18 (59.5 g) in methanol (450 ml) was mixed with formaldehyde solution (37% w/w in water, 173 ml) the solution heated at 70° C. for two hours under nitrogen. This was cooled in an ice-salt bath and sodium borohydride pellets (70.3 g) were added over 2 hours at such a rate that the temperature was kept below 10° C. This solution was stirred to room temperature over 14 h then quenched by the cautious addition of 200 ml of saturated aqueous ammonium chloride to the mixture with ice cooling. The solution volume was reduced to about 200 ml and the residue partitioned between water and DCM and extracted with a second 500 ml portion of DCM. The combined organic fractions were washed with brine, dried over sodium sulfate and purified on a Biotage™ silica column eluting with a gradient of 5% to 10% methanol in DCM containing 0.5% v/v of aqueous ammonia, affording 49.5 g of the title compound as a straw-coloured gum.

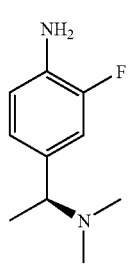

Intermediate 20

4-[(1S)-1-(Dimethylamino)ethyl]-2-fluoroaniline

A solution of Intermediate 19 (1.30 g) in anhydrous methanol (50 ml) was treated with 4M hydrogen chloride in dioxan (11.8 ml) and stirred at ambient temperature for 18 h. The reaction mixture was concentrated under reduced pressure and purified on 2×10 g SCX SPE cartridges eluting with methanol to 1N methanolic ammonia to give the title compound (0.742 g) as yellow oil.

$^1$H NMR (CDCl$_3$) δ: 1.33 (3H, d), 2.19 (6H, s), 3.18 (1H, q), 3.65 (2H, bs), 6.72 (1H, m), 6.85 (1H, m), 6.95 (1H, m)

Intermediate 21

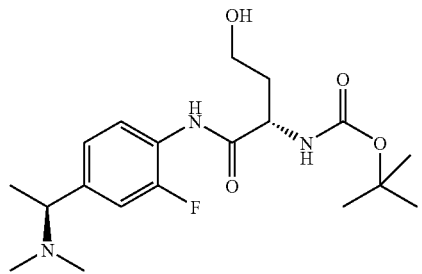

1,1-Dimethylethyl{(1S)-1-[({4-[(1S)-1-(dimethylamino)ethyl]-2-fluorophenyl}amino)carbonyl]-3-hydroxypropyl}carbamate A solution of Intermediate 20 (0.74 g) in dry DCM (20 ml) was stirred at ambient temperature under nitrogen and treated with a 2M solution of trimethylaluminium in heptane (2.5 ml ) over 15 min. The reaction mixture was stirred at 25–27° C.° for 15 min. A solution of 1,1-dimethylethyl [(3S)-2-oxotetrahydro-3-furanyl]carbamate (0.817 g) in dry DCM (5 ml) was added over 15 min. The reaction mixture was stirred at ambient temperature, under nitrogen for 19 h. The reaction mixture was treated with 10% aqueous sodium potassium tartrate (15 ml) over 30 min and filtered through a hydrophobic frit. The aqueous layer was stirred with DCM (50 ml) and filtered through the hydrophobic frit. The combined DCM extracts were concentrated under reduced pressure. The residue was purified by silica SPE eluting with DCM:methanol:2N methanolic ammonia 100:10:1 to give the title compound (0.86 g) as a cream foam.

Mass spectrum: Found: MH$^+$ 384

Intermediate 22

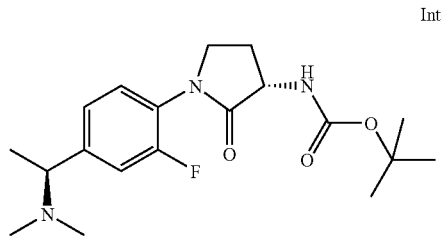

1,1-Dimethylethyl((3S)-1-{4-[(1S)-1-(dimethylamino)ethyl]-2-fluorophenyl}-2-oxo-3-pyrrolidinyl)carbamate A solution of Intermediate 21 (0.855 g) in anhydrous THF (30 ml) was stirred under nitrogen and cooled to 0° C. Tri-n-butylphosphine (0.667 ml) was added followed by 1,1'-(azodicarbonyl)dipiperidine (0.675 g) in four portions over 15 min. The slight suspension was stirred at 0° C. for 30 min giving a thick suspension which was then stirred at ambient temperature for 20 h. The reaction mixture was treated with cyclohexane (75 ml), stirred for 15 min and filtered to remove solid which was washed well with cyclohexane. The filtrate was concentrated under reduced pressure. The residue was purified on a 40 g Biotage™ eluting with 20:1 DCM:methanol. Further purification on a 50 g silica SPE eluting with 50:1 to 10:1 DCM:methanol gradient gave the title compound (0.644 g) product as a pale yellow foam.

Mass spectrum: Found: MH$^+$ 366

Intermediate 23

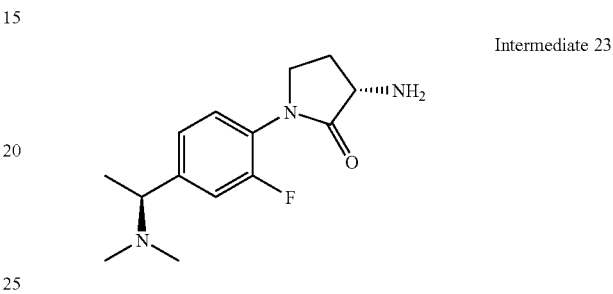

(3S)-3-Amino-1-{4-[(1S)-1-(dimethylamino)ethyl]-2-fluorophenyl}-2-pyrrolidinone

A solution of Intermediate 22 (0.633 g) in methanol (20 ml) was treated with 4M hydrogen chloride in dioxan (2.6 ml) and stirred at ambient temperature for 18 h. The reaction mixture was concentrated under reduced pressure and purified on a 50 g SCX SPE cartridge eluting with methanol and then 2N methanolic ammonia to give the title compound (0.416 g) as a pale yellow oil.

$^1$H NMR (CDCl$_3$) δ: 1.33 (2H, d), 1.95 (1H, m), 2.21 (6H, s), 2.57 (1H, m), 3.23 (1H, m), 3.69 (2H, m), 3.81 (1H, m), 7.11 (2H, m), 7.37 (1H, m).

Intermediate 24

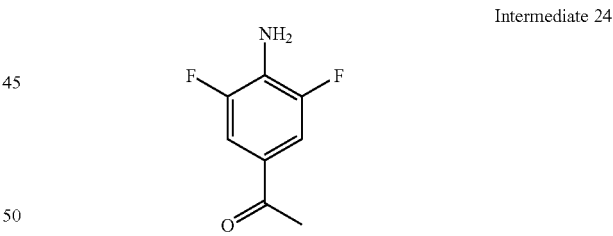

1-(4-Amino-3,5-difluorophenyl)ethanone

A solution of 4-bromo-2,6-difluoroaniline (15 g) in dry DMF (180 ml) was degassed for 30 min. Water (42 ml) was added and the solution was further degassed for 10 min. n-Butyl vinyl ether (46.60 ml), 1,3-bis(diphenylphosphino)propane (1.96 g), potassium carbonate (11.76 g), and palladium (II) acetate (0.48 g) were added and the mixture was stirred at 80° C. under nitrogen for 6 h and then at ambient temperature for 18 h. The mixture was concentrated under reduced pressure. The residue was partitioned between ethyl acetate and water. The separated organic layer was dried over anhydrous sodium sulfate, filtered and concentrated under reduced pressure. The residue was treated with MeCN (100 ml), water (100 ml) and formic acid (2 ml) and stirred at ambient temperature for 45 min. The mixture was concentrated under reduced pressure and partitioned between DCM and saturated aqueous sodium bicarbonate solution. The separated organic layer was dried over anhydrous sodium sulfate, filtered and concentrated under reduced pressure. The residue was purified by flash vacuum chromatography (silica, eluting with ether). Trituration with cyclohexane afforded a solid which was filtered and dried under vacuum at ambient temperature to give the title compound (10.47 g) as a cream solid.

Mass spectrum: Found MH⁺ 172
H.p.l.c. $R_t$ 2.27 min

Intermediate 25

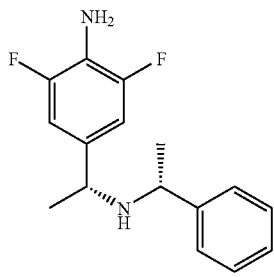

[(1R)-1-(4-Amino-3,5difluorophenyl)ethyl][(1R)-1-phenylethyl]amine

Intermediate 24 (4.43 g) was dissolved in dry toluene (100 ml) and stirred under nitrogen at ambient temperature. (R)-1-phenylethylamine (4 ml) and triethylamine (14.4 ml) were added and then a solution of titanium (IV) chloride (14.24 ml, 1M in toluene) was added dropwise below 25° C. The mixture was stirred at ambient temperature for 20 h. The mixture was filtered and the filtrate was added dropwise to a solution of sodium borohydride (1.95 g) in methanol (200 ml) at −73° C. whilst stirring under nitrogen. The mixture was further stirred for 2.5 h and then quenched with ice water (50 ml) below −25° C. The mixture was warmed to 0° C. and then concentrated under reduced pressure. The residue was partitioned between ethyl acetate and water. The organic layer was separated, dried over anhydrous sodium sulfate, filtered and concentrated under reduced pressure. The residue was purified using Biotage™ chromatography (silica, eluting with cyclohexane:ethyl acetate 9:1) to give the title compound (2.57 g) as a colorless oil.

Mass spectrum: MH⁺ 277.
H.p.l.c. $R_t$ 2.06 min

Intermediate 26

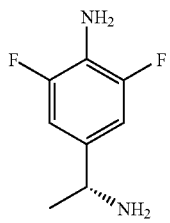

[(1R)-1-(4-Amino-3,5-difluorophenyl)ethyl]amine

Intermediate 25 (2.56 g) was dissolved in absolute ethanol (95 ml) and degassed using a stream of nitrogen at ambient temperature. Ammonium formate (4.78 g) and 10% palladium on carbon (0.50 g) were added and the mixture was heated with stirring at 65° C. for 1.5 h. The mixture was filtered and the filtrate was concentrated under reduced pressure. The residue was purified using Biotage™ chromatography (silica, eluting with cyclohexane:ether, 1:3 to DCM:methanol: aqueous ammonia, 9:1:2% ) to give the title compound (1.22 g) as a pale brown oil.

TLC (silica, chloroform:methanol:aqueous ammonia, 9:1:1) $R_f$ 0.35

Intermediate 27

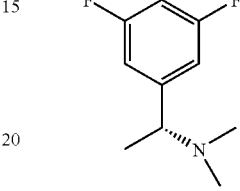

[(1R)-1-(4-Amino-3,5-difluorophenyl)ethyl]dimethylamine

A solution of Intermediate 26 (1.08 g) in dry THF (21.6 ml) was degassed whilst cooling in an ice bath. 37% aqueous formaldehyde (1.08 ml) was added dropwise, followed by sequential addition of sodium triacetoxyborohydride (2.66 g) and glacial acetic acid (0.216 ml). The mixture was stirred at ambient temperature for 21 h. The mixture was concentrated under reduced pressure and the residue was purified using a pre-conditioned SCX SPE cartridge (50 g/150 ml) eluting with 5% aqueous ammonia/methanol and then using Biotage™ chromatography (silica, eluting with chloroform:methanol, 98:2 to 95:5) to give the title compound (0.374 g) as a pale brown oil.

TLC (silica, chloroform:methanol:aqueous ammonia, 9:1:1) $R_f$ 0.16

Intermediate 28

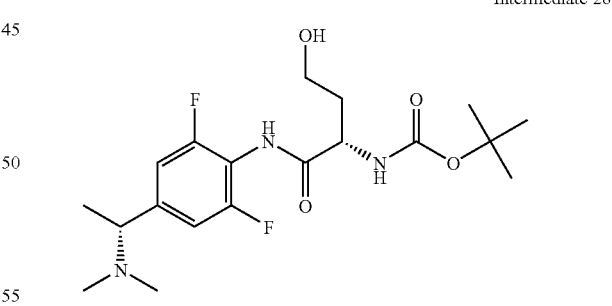

1,1-Dimethylethyl{(1S)-1-[({4-[(1R)-1-(dimethylamino)ethyl]-2,6-difluorophenyl}amino)carbonyl]-3-hydroxypropyl}carbamate A solution of Intermediate 27 (0.374 g) in DCM (4 ml) was degassed at 10° C. in an ice bath. Trimethylaluminium (1.12 ml, 2M in heptane) was added dropwise below 20° C. and the mixture was stirred for 30 min at ambient temperature. A solution of 1,1-dimethylethyl [(3S)-2-oxotetrahydro-3-furanyl]carbamate (0.38 g) in DCM (4 ml) was added dropwise below 25° C. The mixture was stirred at ambient temperature for 20 h. A further portion of trimethylaluminium (1.12 ml, 2M in heptane) was added and the mixture was heated at reflux for 2 h. The mixture was cooled in an ice bath and then 10% aqueous sodium potassium tartrate (7 ml) was added dropwise over 10 min. The mixture was diluted with DCM. The separated organic layer was passed through a hydrophobic frit and concentrated under reduced pressure. The residue was purified using Biotage™ chromatography (silica, gradient eluting with chloroform:methanol, 9:1 to chloroform:methanol: aqueous ammonia, 9:1:1%) to give the title compound (0.635 g) as a white solid.

Mass spectrum: Found: MH+ 402
H.p.l.c. R$_t$ 1.84 min.

Intermediate 29

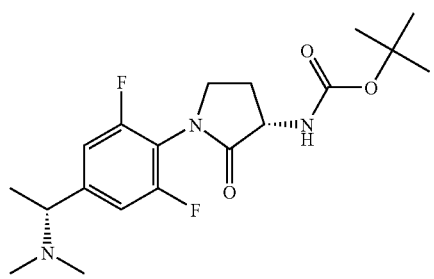

1,1-Dimethylethyl((3S)-1-{4-[(1R)-1-(dimethylamino)ethyl]-2,6-difluorophenyl}-2-oxo-3-pyrrolidinyl)carbamate To a solution of Intermediate 28 (0.635 g) in dry THF (14 ml) under nitrogen at 0° C. was added solid 1,1'(azodicarbonyl)-dipiperidine (0.48 g) and tri-n-butylphosphine (0.47 ml). The solution was allowed to warm to ambient temperature and stirred for 18 h. The mixture was concentrated under reduced pressure and the residue was partitioned between DCM and aqueous saturated sodium bicarbonate. The organic layer was passed through a hydrophobic frit and concentrated under reduced pressure. The residue was purified using Biotage™ chromatography (silica, gradient eluting with DCM to chloroform:methanol, 95:5 to 90:10:1% aqueous ammonia) to give the crude title compound (0.899 g) as an orange oil.

Mass spectrum: Found: MH+ 384
H.p.l.c. R$_t$ 2.04 min.

Intermediate 30

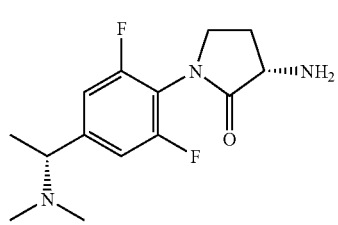

(3S)-3-Amino-1-{4-[(1R)-1-(dimethylamino)ethyl]-2,6-difluorophenyl}-2-pyrrolidinone Intermediate 29 (0.899 g) was stirred in dry DCM (9 ml) and trifluoroacetic acid (2.47 ml) under nitrogen at ambient temperature for 2 h. The mixture was concentrated under reduced pressure. The residue was purified using SCX SPE (20 g/60 ml) eluting with DCM to 5% aqueous ammonia/methanol to give the title compound (0.036 g) as a pale brown oil.

Mass spectrum: Found: MH+ 284
H.p.l.c. R$_t$ 2.06 min

Intermediate 31

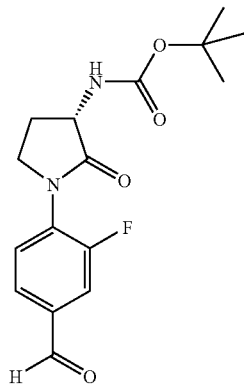

1,1-Dimethylethyl (3S)-1-(2-fluoro-4-formylphenyl)-2-oxopyrrolidin-3-ylcarbamate Carbon monoxide was bubbled through a mixture of Intermediate 2 (4 g), palladium (II) acetate (0.106 g) and 1,1'-bis(diphenylphosphino)ferrocene (0.527 g) in DMF (50 ml) for 10 min. Triethylamine (3.3 ml) was added in one portion followed by triethylsilane (3 ml) added dropwise over 1 h. The mixture was heated at 80° C. for 1 h. More, palladium (II) acetate (0.53 g), 1,1'-bis(diphenylphosphino) ferrocene (0.263 g), triethylamine (1.65 ml) and triethylsilane (1.5 ml) were then added. More carbon monoxide was babbled through the mixture for 10 min. The mixture was heated under the carbon monoxide atmosphere for a further 2 h. The cooled reaction mixture was quenched with brine (500 ml) and extracted with ethyl acetate (250 ml). The organic extract was washed with brine (200 ml), dried (magnesium sulfate) and evaporated under reduced pressure. The residue was purified on a silica SPE eluting with cyclohexane: ethyl acetate (3:1 to 13:7) to give the title compound (1.42 g) as a creamy white solid.

Mass spectrum: Found: MH+ 323
H.p.l.c. R$_t$ 2.65 min

Intermediate 32

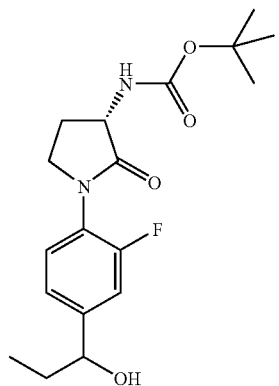

1,1-Dimethylethyl(3S)-1-[2-fluoro-4-(1-hydroxypropyl)phenyl]-2-oxopyrrolidin-3-ylcarbamate To a solution of Intermediate 31 (0.05 g) in dry THF (1.5 ml) at 0° C. under nitrogen, was added a solution of ethylmagnesium chloride in THF (2M, 0.17 ml) dropwise and stirred for 3 h. The reaction was quenched at 0° C. with saturated aqueous ammonium chloride (1 ml), extracted with ethyl acetate (2X), dried, and evaporated under educed pressure. The residue was purified on a silica SPE eluted with cyclohexane: ethyl acetate (1:1 to 1:3) and then 100% ethyl acetate to give the title compound (0.038 g).

Mass spectrum: Found: MH$^+$ 353

H.p.l.c. R$_t$ 2.68 min

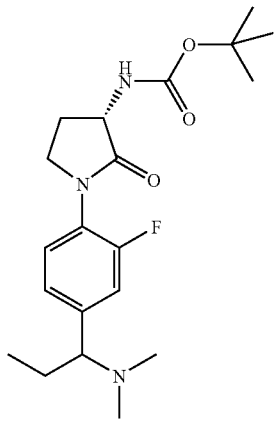

Intermediate 33

1,1-Dimethylethyl((3S)-1-{4-[1-(dimethylamino) propyl]-2-fluorophenyl}-2-oxo-3-pyrrolidinyl)carbamate Intermediate 32 (0.038 g) in dry DCM (1 ml) at 0° C. was treated with triphenylphosphine (0.033 g) and carbon tetrabromide (0.043 g). The reaction was warmed up to ambient temperature and stirred for 2 h under nitrogen. The mixture was evaporated under reduced pressure. The residue was treated with 2N dimethylamine in THF (1 ml) and stirred at ambient temperature overnight. Solvent was removed under reduced pressure and the residue partitioned between DCM and saturated aqueous sodium bicarbonate solution. The separated organic layer was passed through a hydrophobic frit and re-concentrated under reduced pressure. The residue was purified using SCX SPE (eluting with methanol to 10% ammonia/methanol to give the title compound (0.031 g).

Mass spectrum: Found: MH$^+$ 380

H.p.l.c. R$_t$ 2.13 min

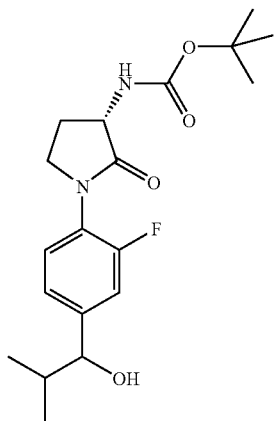

Intermediate 34

1,1-Dimethylethyl(3S)-1-[2-fluoro-4-(1-hydroxy-2-methylpropyl)phenyl]-2-oxopyrrolidin-3-ylcarbamate The title compound was prepared from Intermediate 31, and isopropylmagnesium chloride using the procedure described for Intermediate 32.

Mass spectrum: Found: MH$^+$ 367

H.p.l.c. R$_t$ 2.91 min

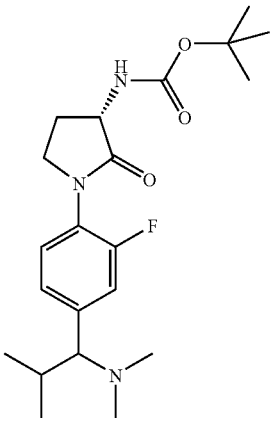

Intermediate 35

1,1-Dimethylethyl((3S)-1-{4-[1-(dimethylamino)-2-methylpropyl]-2-fluorophenyl}-2-oxo-3-pyrrolidinyl)carbamate Intermediate 34 (0.064 g) in dry DCM (1.7 ml) at 0° C. was treated with triphenylphosphine (0.055 g) and carbon tetrabromide (0.070 g). The reaction was warmed up to ambient temperature and stirred for 2 h under nitrogen. The mixture was evaporated under reduced pressure. The residue was treated with sodium iodide (0.003 g), 2N dimethylamine in THF (3 ml) and dimethoxyethane (1 ml). The mixture was heated at 50° C. under nitrogen overnight. The cooled reaction mixture was evaporated under reduced pressure and the residue partitioned between DCM and saturated aqueous sodium bicarbonate solution. The separated organic layer was passed through a hydrophobic frit and re-concentrated under reduced pressure. The residue was purified using SCX SPE (eluting with methanol to 10% ammonia/methanol to give the title compound (0.021 g).

Mass spectrum: Found: MH$^+$ 394

H.p.l.c. R$_t$ 2.22 min

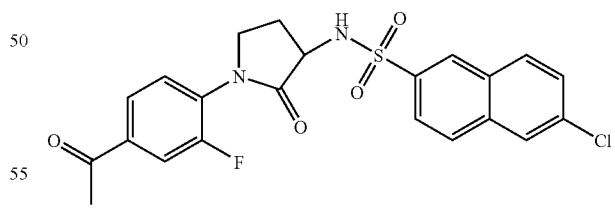

Intermediate 36

N-[1-(4-Acetyl-2-fluorophenyl)-2-oxo-3-pyrrolidinyl]-6-chloro-2-naphthalenesulfonamide The title compound was prepared from Intermediate 7 and 6-chloro-2-naphthalene sulfonyl chloride using the procedure described for Intermediate 8.

Mass spectrum: Found: MH$^+$ 461

H.p.l.c. R$_t$ 3.37 min

Intermediate 37

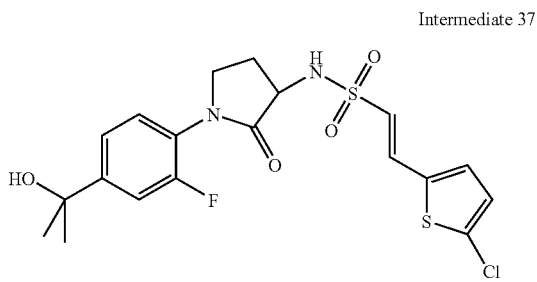

(E)-2-(5-Chloro-2-thienyl)-N-{1-[2-fluoro-4-(1-hydroxy-1-methylethyl)phenyl]-2-oxo-3-pyrrolidinyl}ethenesulfonamide Titanium (IV) chloride (1M in DCM, 6.7 ml) was added dropwise to anhydrous diethyl ether (25 ml) at −78° C. Dimethyl zinc (1M in heptane, 6.7 ml) was then added, keeping the temperature <−50° C. The mixture was allowed to warm to −30° C., and Intermediate 8 (990 mg) was added dropwise as an anhydrous DCM solution (25 ml). The mixture was then stirred for three hours at −20° C. to −5° C., then quenched by addition to cold water. The mixture was extracted with diethyl ether, and the organic extracts dried (magnesium sulfate) and concentrated under reduced pressure to give the title compound (1.03 g).
Mass spectrum: Found: MH+ 459
H.p.l.c. $R_t$ 3.15 min Intermediate 38

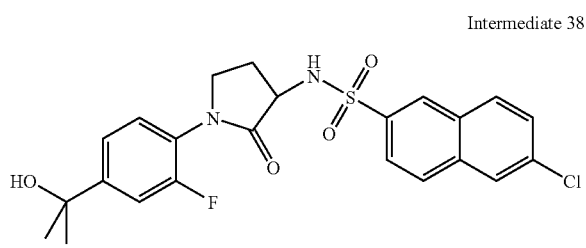

6-Chloro-N-{1-[2-fluoro-4-(1-hydroxy-1-methylethyl)phenyl]-2-oxo-3-pyrrolidinyl}-2-naphthalenesulfonamide The title compound was prepared from Intermediate 36 using the procedure described for Intermediate 37.
Mass spectrum: Found: MH+ 477
H.p.l.c. $R_t$ 3.31 min Intermediate 39

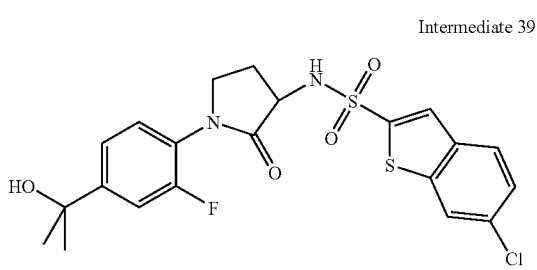

6-Chloro-N-{1-[2-fluoro-4-(1-hydroxy-1-methylethyl)phenyl]-2-oxo-3-pyrrolidinyl}-1-benzothiophene-2-sulfonamide The title compound was prepared from Intermediate 12 using the procedure described for Intermediate 37.

Mass spectrum: Found: MH+ 483
H.p.l.c. $R_t$ 3.34 min

Intermediate 40

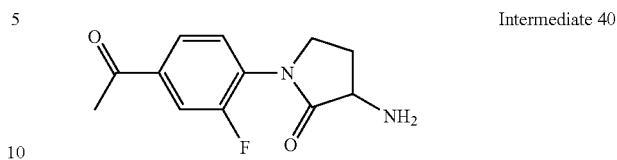

1-(4-Acetyl-2-fluorophenyl)-3-amino-2-pyrrolidinone

To a solution of 4-amino-3-fluoro-acetophenone (2.43 g) in MeCN (60 ml) at 0° C. under nitrogen, was added sodium phosphate (1.43 g). The resulting mixture was treated dropwise with 2,4-dibromobutanoyl chloride (2.4 ml) and stirred for 1 h. Potassium carbonate (4.38 g) was added and the mixture stirred for 18 h, warming gradually to room temperature. The mixture was filtered through celite filter-aid, washed with MeCN (10 ml) and the combined filtrates treated with 0.880 aqueous ammonia (30 ml). The mixture was heated to 40° C. for 20 h, then concentrated under reduced pressure, partitioning the residue between DCM and saturated aqueous sodium bicarbonate. The separated organic layer was passed through a hydrophobic frit and concentrated under reduced pressure to give an orange oil which was purified by Biotage™ silica chromatography eluting with 400:10:1 then 200:10:1 DCM:Methanol:0.880 aqueous ammonia to give the title compound (3.06 g) as a yellow oil.
Mass spectrum: Found: MH+ 237
H.p.l.c. $R_t$ 0.84 min Intermediate 41

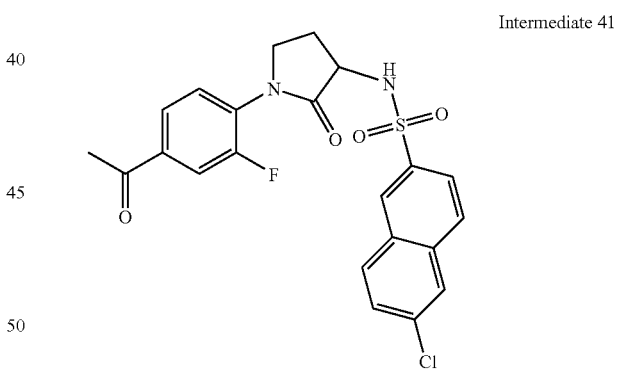

N-[1-(4-Acetyl-2-fluorophenyl)-2-oxo-3-pyrrolidinyl]-6-chloro-2-naphthalenesulfonamide A suspension of Intermediate 40 (1.0 g) in dry MeCN (40 ml) was cooled to 0° C. under nitrogen and treated with pyridine (0.685 ml). 6-Chloro-2-naphthalenesulfonyl chloride (1.31 g) was added portionwise over 20 min and the reaction mixture was stirred in the cooling bath for 4 h and then stirred at ambient temperature for 18 h. The mixture was concentrated under reduced pressure and the residue was purified by Biotage™ silica chromatography eluting with a gradient of 3:1 to 1:1 cyclohexane:ethylacetate to give the title compound (1.37 g) as a yellow solid.

Intermediate 42

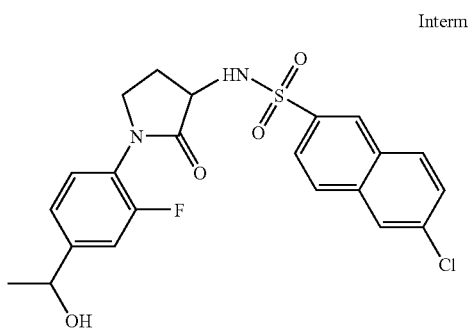

6-Chloro-N-{1-[2-fluoro-4-(1-hydroxyethyl)phenyl]-2-oxo-3-pyrrolidinyl}-2-naphthalenesulfonamide Intermediate 41 (1.36 g) in dry methanol (30 ml) was at 0° C. treated with sodium borohydride (0.223 g) and the mixture stirred at ambient temperature for 18 h under nitrogen. Additional sodium borohydride (0.07 g) was added and the reaction stirred for a further 3 h. The reaction was quenched with aqueous ammonium chloride (10 ml) and concentrated under reduced pressure, partitioning the residue between DCM and saturated aqueous sodium bicarbonate. The separated organic layer was passed through a hydrophobic frit and concentrated under reduced pressure to give the title compound (1.40 g) as a pale yellow foam.

Mass spectrum: Found: MH+ 463
H.p.l.c. $R_t$ 3.14 min

Intermediate 43

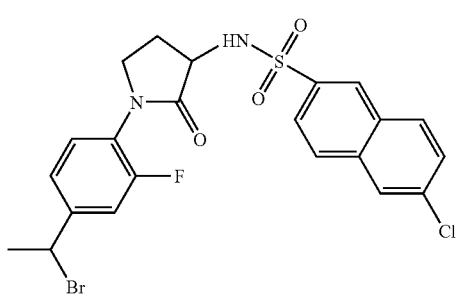

N-{1-[4-(1-Bromoethyl)-2-fluorophenyl]-2-oxo-3-pyrrolidinyl}-6-chloro-2-naphthalenesulfonamide Intermediate 42 (1.37 g) in dry DCM (40 ml) at 0° C. was treated with triphenylphosphine (1.07 g) and stirred for 40 min. To the mixture was added N-bromo-succinimide (0.65 g) and the reaction stirred at 0–10° C. for 1 h then at ambient temperature for 2 h. Additional triphenylphosphine (0.60 g) was added followed by additional N-bromo-succinimide (0.45 g) and the reaction stirred for 18 h. The reaction mixture was applied directly to a pre-conditioned silica SPE (50 g), eluting with 3:1 then 1:1 cyclohexane:ethylacetate to give the title compound (1.44 g) as a pink foam.

Mass spectrum: Found: MH+ 525
H.p.l.c. $R_t$ 3.61 min

Intermediate 44

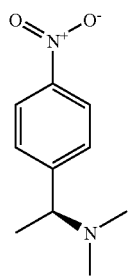

(1S)-N,N-Dimethyl-1-(4-nitrophenyl)ethanamine

The title compound was prepared from free-based (1S)-1-(4-nitrophenyl)ethanamine using the procedure described for Intermediate 19.

Mass spectrum: Found: MH+ 195
H.p.l.c. $R_t$ 0.8 min

Intermediate 45

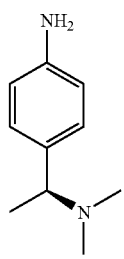

4-[(1S)-1-(Dimethylamino)ethyl]aniline

A solution of intermediate 44 (0.78 g) in ethanol (20 ml) containing 10% palladium on charcoal (0.025 g) was stirred under an atmosphere of hydrogen for 4 h. The catalyst was filtered and the solvent evaporated prior to purification by silica chromatography, eluting with 10% methanol in chloroform containing 0.5% aqueous ammonia, which afforded (0.55 g) of the title compound as a colourless oil.

Mass spectrum: Found: MH+ 165
H.p.l.c. $R_t$ 0.2 min

Intermediate 46

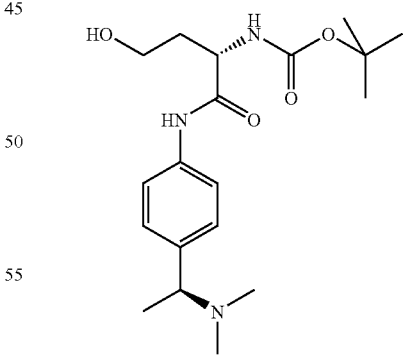

1,1-Dimethylethyl{(1S)-1-[({4-[(1S)-1-(dimethylamino)ethyl]phenyl}amino)carbonyl]-3-hydroxypropyl}carbamate The title compound was prepared from intermediate 45 using the procedure described for Intermediate 1.

Mass spectrum: Found: MH+ 366
H.p.l.c. $R_t$ 1.82 min

Intermediate 47

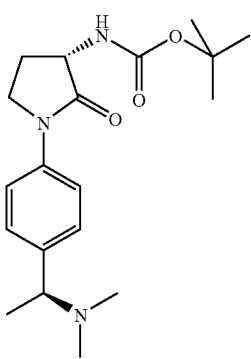

1,1-Dimethylethyl((3S)-1-{4-[(1S)-1-(dimethy-lamino)ethyl]phenyl}-2-oxo-3-pyrrolidinyl)carbamate The title compound was prepared from intermediate 46 using the procedure described for Intermediate 2.

Mass spectrum: Found: MH⁺ 348

H.p.l.c. $R_t$ 1.98 min

Intermediate 48

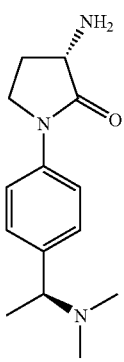

(3S)-3-Amino-1-{4-[(1S)-1-(dimethylamino)ethyl]phenyl}-2-pyrrolidinone

The title compound was prepared from Intermediate 47 using the procedure described for Intermediate 23

Mass spectrum: Found: MH⁺ 248

H.p.l.c. $R_t$ 0.2 min

Intermediate 49

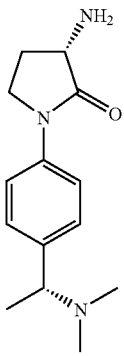

(3S)-3-Amino-1-{4-[(1R)-1-(dimethylamino)ethyl]phenyl}-2-pyrrolidinone

The title compound was prepared from (1R)-1-(4-nitrophenyl)ethanamine using the procedures described for Intermediates 44 to 48.

Mass spectrum: Found: MH⁺ 248

H.p.l.c. $R_t$ 0.2 min

Intermediate 50

3-Amino-1-(4-bromo-2,6-difluorophenyl)-2-pyrrolidinone

The title compound was prepared from 4-bromo-2,6-difluoroaniline using the procedure described for Intermediate 40.

Mass spectrum: Found: MH⁺ 291/293

H.p.l.c. $R_t$ 1.55 min

Intermediate 51

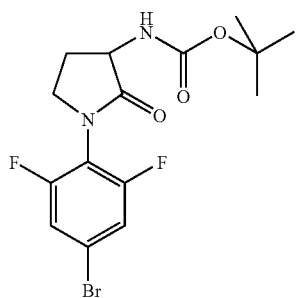

1,1-Dimethylethyl[1-(4-bromo-2,6-difluorophenyl)-2-oxo-3-pyrrolidinyl]carbamate

A solution of Intermediate 50 (2.9 g) in DCM (100 ml) was treated with bis(1,1-dimethylethyl) dicarbonate (2.4 g) and the mixture stirred for 84 h at room temperature. The crude solution was directly loaded onto 2×90 g silica cartridges and these were eluted with 1:3 ethyl acetate:cyclohexane, to give the title compound (3.1 g) as a white solid.

Mass spectrum: Found: MH⁺ 391/393

H.p.l.c. $R_t$ 3.07 min

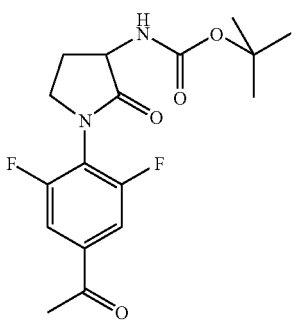

1,1-Dimethylethyl[1-(4-acetyl-2,6-difluorophenyl)-2-oxo-3-pyrrolidinyl]carbamate

The title compound was prepared from Intermediate 51 using the procedure described for Intermediate 3
Mass spectrum: Found: MH⁺ 355
H.p.l.c. $R_t$ 2.78 min

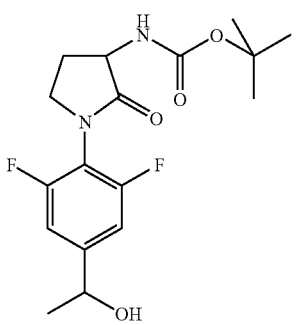

1,1-Dimethylethyl{1-[2,6-difluoro-4-(1-hydroxyethyl)phenyl]-2-oxo-3-pyrrolidinyl}carbamate

The title compound was prepared from intermediate 52 using the procedure described for Intermediate 9.
Mass spectrum: Found: MH⁺ 357
H.p.l.c. $R_t$ 2.64 min

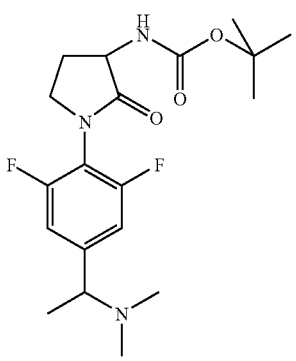

1,1-Dimethylethyl(1-{4-[1-(dimethylamino)ethyl]-2,6-difluorophenyl}-2-oxo-3-pyrrolidinyl)carbamate

A solution of Intermediate 53 (0.305 g) in DCM (20 ml) and cooled to 0° C. was treated with methanesulphonyl chloride (0.099 ml) and triethylamine (0.179 ml) and stirred for 15 min at that temperature. Dimethylamine (2M solution in THF, 2.5 ml) was added to this and the mixture stirred overnight at room temperature. Another aliquot of the dimethylamine solution (2.5 ml) was added and stirring continued at room temperature for another 24 h when all volatiles were removed. The residue was purified using pre-conditioned silica SPE (10 g/50 cc) eluting with ethyl acetate, then 10% methanol In chloroform containing 0.5% aqueous ammonia, to give the title compound (0.225 g) as a colourless oil.
Mass spectrum: Found: MH⁺ 384
H.p.l.c. $R_t$ 2.09 min

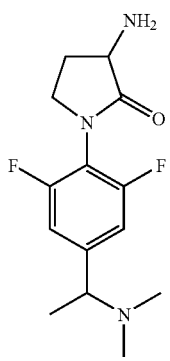

3-Amino-1-{4-[1-(dimethylamino)ethyl]-2,6-difluorophenyl}-2-pyrrolidinone

The title compound was prepared from Intermediate 54 using the procedure described for Intermediate 30.
Mass spectrum: Found: MH⁺ 284
H.p.l.c. $R_t$ 0.2 min

EXAMPLE 1

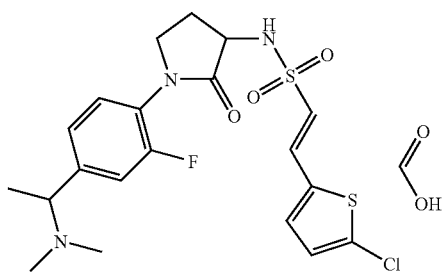

(E)-2-(5-Chloro-2-thienyl)-N-(1-{4-[1-(dimethylamino)ethyl]-2-fluorophenyl}-2-oxo-3-pyrrolidinyl)ethenesulfonamide formate (alternatively known as Formic acid—(E)-2-(5-chloro-2-thienyl)-N-(1-{4-[1-(dimethylamino)ethyl]-2-fluorophenyl}-2-oxo-3-pyrrolidinyl)ethenesulfonamide (1:1))

Intermediate 6 (0.019 g) was stirred in 4M hydrogen chloride/dioxan (3 ml) at ambient temperature for 2 h. The reaction was concentrated under reduced pressure to give an off white gum (0.019 g). This material in dry MeCN (2 ml) at 0° C. was treated with DIPEA (0.031 ml). The reaction was stirred for 5 min before a pre-cooled solution of (E)-2-(5-chloro-2-thienyl)ethenesulfonyl chloride (0.0136 g) in dry MeCN (2 ml) was added in dropwise manner. Upon completion of addition, the mixture was stirred at 0° C. for 2 h, then warmed up and stirred at room temperature for 6 h under nitrogen. Solvent was removed under reduced pressure and the residue partitioned between DCM and saturated aqueous sodium bicarbonate solution. The separated organic layer was washed with water, passed through a hydrophobic frit and concentrated under reduced pressure. The residue was purified by mass directed preparative h.p.l.c. to give the title compound (0.021 g) as a white powder.

Mass spectrum: Found: MH$^+$ 472

H.p.l.c. R$_t$ 2.38 min

EXAMPLE 1 (ALTERNATIVE PROCEDURE)

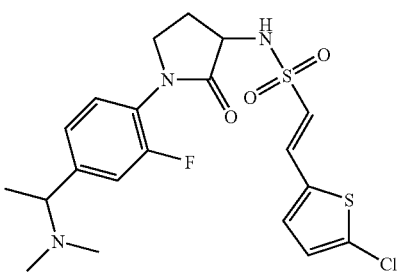

(E)-2-(5-Chloro-2-thienyl)-N-(1-{4-[1-(dimethylamino)ethyl]-2-fluorophenyl}-2-oxo-3-pyrrolidinyl)ethenesulfonamide

GSK201106B

Intermediate 10 (0.066 g) in dry THF (4 ml) was treated with a 2N solution of dimethylamine in THF (0.143 ml). The reaction was stirred at room temperature for 1.5 h. After this period the reaction was heated to 45° C. for 3 h, before cooling to room temperature and stirring for 72 h. The mixture was concentrated under reduced pressure, partitioning the residue between DCM and saturated aqueous sodium bicarbonate solution. The separated organic layer was washed with water, passed through a hydrophobic frit and concentrated under reduced pressure. The residue was loaded onto a pre-conditioned SCX SPE cartridge (2 g/12 cc) eluting the product with 10% aqueous ammonia/methanol to give the title compound (0.021 g) as a pink gummy solid.

Mass spectrum: Found: MH$^+$ 472

H.p.l.c. R$_t$ 2.34 min

EXAMPLE 2

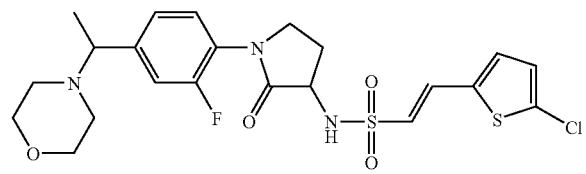

(E)-2-(5-Chloro-2-thienyl)-N-(1-{2-fluoro-4-[1-(4-morpholinyl)ethyl]phenyl}-2-oxo-3-pyrrolidinyl)ethenesulfonamide

GSK208232A

A solution of Intermediate 10 (30 mg) in dry THF (3 ml) was treated with morpholine (26 ul). The mixture was heated to 45° C. for 18 h, before allowing cooling to ambient temperature. Solvent was removed under reduced pressure and the residue partitioned between chloroform and saturated aqueous sodium bicarbonate solution. The separated organic layer was passed through a hydrophobic frit and re-concentrated under reduced pressure. The residue was purified by mass directed preparative h.p.l.c. to give the title compound (0.018 g) as a white powder.

Mass spectrum: Found: MH$^+$ 514

H.p.l.c. R$_t$ 2.42 min

EXAMPLE 3

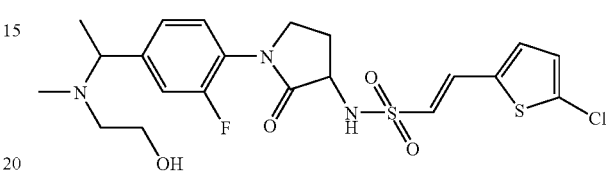

(E)-2-(5-Chloro-2-thienyl)-N-[1-(2-fluoro-4-{1-[(2-hydroxyethyl)(methyl)amino]ethyl}phenyl)-2-oxo-3-pyrrolidinyl]ethenesulfonamide

GSK208233A

The title compound was prepared from intermediate 10 and ethanolamine using the procedure described in Example 2.

Mass spectrum: Found: MH$^+$ 502

H.p.l.c. R$_t$ 2.36 min

EXAMPLE 4

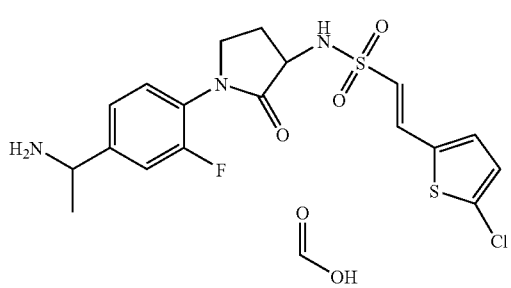

(E)-N-{1-[4-(1-Aminoethyl)-2-fluorophenyl]-2-oxo-3-pyrrolidinyl}-2-(5-chloro-2-thienyl)ethenesulfonamide formate

GW 870017A

Intermediate 11 (0.065 g) was treated with 6N aqueous hydrochloric acid (5 ml). The mixture was stirred at ambient temperature for 18 h, then heated to 50° C. for 3 h, before allowing cooling to ambient temperature. Solvent was removed under reduced pressure and the residue partitioned between DCM and saturated aqueous sodium bicarbonate solution. The separated organic layer was passed through a hydrophobic frit and re-concentrated under reduced pressure. The residue was purified by mass directed preparative h.p.l.c. to give the title compound (0.011 g) as a white powder.

Mass spectrum: Found: MH$^+$ 444

H.p.l.c. R$_t$ 2.40 min

EXAMPLE 5

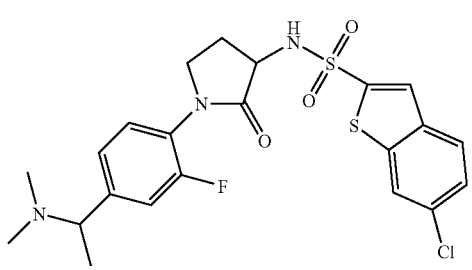

6-Chloro-N-(1-{4-[1-(dimethylamino)ethyl]-2-fluorophenyl}-2-oxo-3-pyrrolidinyl)-1-benzothiophene-2-sulfonamide

GSK242208A

The title compound was prepared from Intermediate 14 at room temperature using a similar synthetic procedure to that described for Example 1 (alternative procedure).
Mass spectrum: Found: MH+ 496
H.p.l.c. $R_f$ 2.44 min

EXAMPLE 6

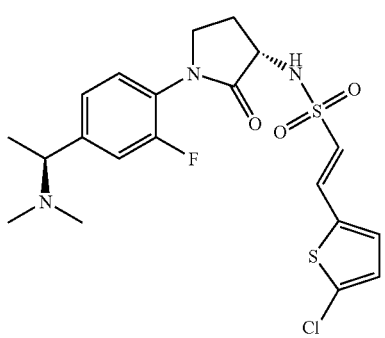

(E)-2-(5-Chloro-2-thienyl)-N-((3S)-1-{4-[(1S)-1-(dimethylamino)ethyl]-2-fluorophenyl}-2-oxo-3-pyrrolidinyl)ethenesulfonamide

GSK327898A

A solution of Intermediate 23 (0.10 g) in dry MeCN (5 ml) was cooled to 0° C. under nitrogen and treated with DIPEA (131 ul). A solution of (E)-2-(5-chloro-2-thienyl)ethenesulfonyl chloride (0.11 g) in dry MeCN (2 ml) was added slowly over 15 min. The reaction mixture was left stirring in the ice bath for 1 h and the stirred at ambient temperature for 18 h covered in foil. The mixture was concentrated under reduced pressure and the residue was partitioned between DCM (15 ml, 10 ml) and saturated aqueous sodium bicarbonate (10 ml). The separated organic extracts were combined, washed with saturated aqueous sodium chloride, passed through a hydrophobic frit and concentrated under reduced pressure. The residue was purified on a 20 g silica SPE cartridge eluting with DCM: methanol gradient (50:1 to 20:1) to give the title compound (0.104 g) as a light brown foam.
Mass spectrum: Found: MH+ 472
$^1$H NMR (CDCl$_3$) δ: 1.32 (3H, d), 2.05 (6H, s), 2.26 (1H, m), 2.75 (1H, m), 3.23 1H, m), 3.72 (1H, t), 3.85 (1H, m), 4.14 (1H, m), 5.14 (1H, bs), 6.60 (1H, d), 6.90 (1H, d), 7.08 (1H, d, 1H), 7.12 (2H, m), 7.32 (1H, m, 1H), 7.51 (1H, d, 1H)
Hplc Chiralpak AD, 215 nm, 15% EtOH/heptane 1.00 ml/min $R_t$ 45.25 min

EXAMPLE 7

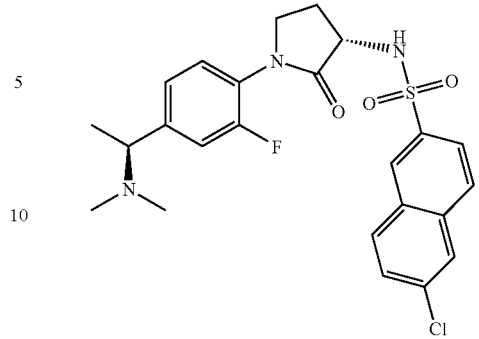

6-Chloro-N-((3S)-1-{4-[(1S)-1-(dimethylamino)ethyl]-2-fluorophenyl}-2-oxo-3-pyrrolidinyl)-2-naphthalenesulfonamide

GSK339796A

A solution of Intermediate 23 (0.050 g) in dry MeCN (5 ml) was cooled to 0° C. under nitrogen and treated with DIPEA (65.6 ul). Solid 6-chloro-2-naphthalenesulfonyl chloride (0.059 g) was added in two portions over 10 min and the reaction mixture was stirred in the cooling bath for 2 h and then stirred at ambient temperature for 18 h. The mixture was concentrated under reduced pressure and the residue was partitioned between DCM and saturated aqueous sodium bicarbonate. The separated organic extracts were combined, washed with saturated aqueous sodium chloride, passed through a hydrophobic frit and concentrated under reduced pressure. The residue was purified on a 20 g silica SPE cartridge eluting with DCM:methanol gradient (33:1 to 20:1) to give the title compound (0.065 g) as a colourless solid.
Mass spectrum: Found: MH+ 490
$^1$H NMR (CDCl$_3$) δ: 1.30 (3H, d), 2.18 (6H, s, 6H), 2.26 (1H, m), 2.75 (1H, m), 3.20 (1H, m), 3.69 (1H, t), 3.79 (1H, m), 3.92 (1 h, m), 5.45 (1H, bs), 7.09 (2H, m), 7.26 (m, 2H), 7.57 (1H, dd), 7.93 (3H, m), 8.49 (1H, s)
Hplc Chiralcel OJ, 215 nm, 25% EtOH/heptane 1.00 ml/min $R_t$ 15.27 min

EXAMPLE 8

GSK335090A

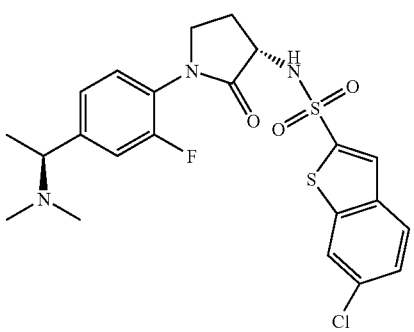

6-Chloro-N-((3S)-1-{4-[(1S)-1-(dimethylamino)ethyl]-2-fluorophenyl}-2-oxo-3-pyrrolidinyl)-1-benzothiophene-2-sulfonamide A solution of Intermediate 23 (0.05 g) in dry MeCN (5 ml) was cooled to 0° C. under nitrogen and treated with DIPEA (65.6 ul). Solid 6-chloro-1-benzothiophene-2-sulfonyl chloride (0.060 g) was added in four portions over 10 min and the reaction mixture was stirred in the cooling bath for 2 h and then stirred at ambient temperature for 18 h. The mixture was concentrated under reduced pressure and the residue was partitioned between DCM and saturated aqueous sodium bicarbonate. The separated organic extracts were combined, washed with saturated aqueous sodium chloride, passed through a hydrophobic frit and concentrated under reduced pressure. The residue was purified on a 20 g silica SPE cartridge eluting with DCM:methanol gradient (33:1 to 20:1). The residue was partitioned between saturated aqueous sodium carbonate and DCM. The organic extracts were combined and washed with aqueous saturated sodium chloride, passed through a hydrophobic frit and concentrated under reduced pressure. The residue was purified on a 10 g SCX SPE cartridge eluting with methanol to 2N methanolic ammonia to give the title compound (0.064 g) as a cream foam.

Mass spectrum: Found: MH+ 496

$^1$H NMR (CDCl$_3$) δ: 1.31(3H, d), 2.19 (6H, s), 2.31 (1H, m), 2.79 (1H, m), 3.21 (1H, m), 3.71 (1H, m), 3.83 (1H, m), 4.08 (1H, m), 5.53 (1H, bs), 7.11 (2H, m), 7.29 (1H, m), 7.43 (1H, dd), 7.82 (2H, m), 7.93 (1H, s)

Using (R)-1-phenylethylamine in the imine formation (Intermediate 17), Examples 9, 10 and 11 were prepared in an analogous manner to Examples 6, 7 and 8.

EXAMPLE 9

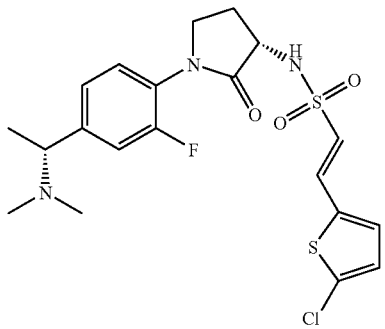

(E)-2-(5-Chloro-2-thienyl)-N-((3S)-1-{4-[(1R)-1-(dimethylamino)ethyl]-2-fluorophenyl}-2-oxo-3-pyrrolidinyl)ethenesulfonamide

GSK327458A

Mass spectrum: Found MH+ 472

$^1$H NMR (CDCl$_3$) δ: 1.39 (3H, bm), 2.28 (7H, m), 2.75 (1H, m), 3.25–3.35 (1H, bm), 3.72 (1H, t), 3.85 (1H, m), 4.14 (1H, m), 5.13 (1H, bs), 6.59 (1H, d), 6.90 (1H, d), 7.09 (1H, d), 7.18 (2H, m), 7.35 (1H, m), 7.52 (1H, d)

Hplc Chiralpak AD, 215 nm, 15% EtOH/heptane 1.00 ml/min R$_t$ 39.77 min

EXAMPLE 10

GSK337702A

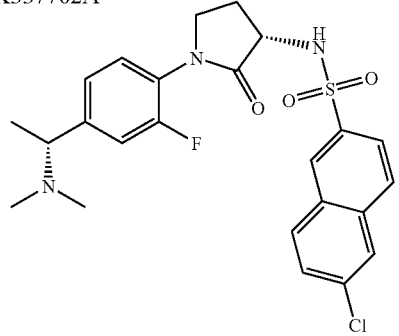

6-Chloro-N-((3S)-1-{4-[(1R)-1-(dimethylamino)ethyl]-2-fluorophenyl}-2-oxo-3-pyrrolidinyl)-2-naphthalenesulfonamide Mass spectrum: Found: MH+ 490

$^1$H NMR (CDCl$_3$) δ: 1.37 (3H, bm), 2.25 (7H, m), 2.75 (1H, m), 3.25–3.35 (1H, bm), 3.69 (1H, t), 3.79 (1H, m), 3.92 (1H, m), 5.47 (1H, bs), 7.13 (2H, bs), 7.30 (2H, m), 7.58 (1H, dd), 7.93 (3H, m), 8.50 (1H, s)

EXAMPLE 11

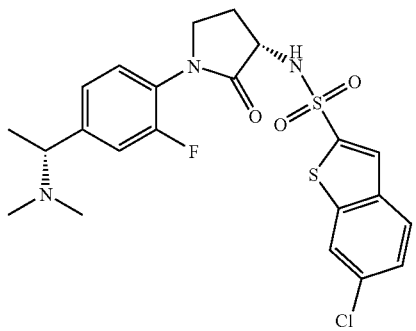

6-Chloro-N-((3S)-1-{4-[(1R)-1-(dimethylamino)ethyl]-2-fluorophenyl}-2-oxo-3-pyrrolidinyl)-1-benzothiophene-2-sulfonamide

GSK337701A

Mass spectrum: Found: MH+ 496

$^1$H NMR (CDCl$_3$) δ 1.40 (3H, m), 2.29 (7H, s), 2.80 (1H, m), 3.30 (1H, bm), 3.73 (1H, m), 3.85 (1H, m), 4.09 (1H, m), 5.57 (1H, bs), 7.19 (2H, bm), 7.35 (1H, bm), 7.45 (1H, dd), 7.83 (2H, m), 7.93 (1H, s)

EXAMPLE 12

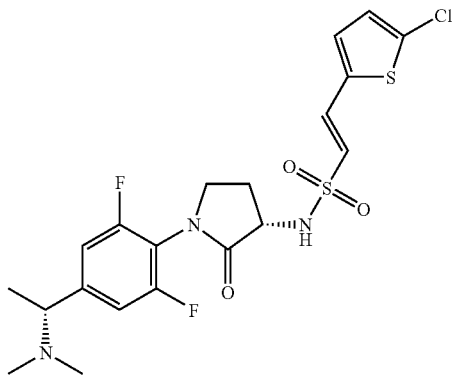

(E)-2-(5-Chloro-2-thienyl)-N-((3S)-1-{4-[(1R)-1-(dimethylamino)ethyl]-2,6-difluorophenyl}-2-oxo-3-pyrrolidinyl)ethenesulfonamide A solution of Intermediate 30 (0.036 g) In dry acetonitrile (1.74 ml), and DIPEA (0.045 ml) was cooled to 0° C. (E)-2-(5-chloro-2-thienyl)ethenesulfonyl chloride (0.031 g) was added and the mixture was shaken on a shaker-bed at ambient temperature for 18 h and then concentrated under reduced pressure. The residue was partitioned between DCM and water. The organic layer was passed through a hydrophobic frit and concentrated using a stream of nitrogen. The residue was purified using pre-conditioned silica SPE (10 g/60 ml) eluting with DCM to DCM:methanol, 90:10) to give the title compound (0.01 g) as a pale brown oil.

Mass spectrum: Found: MH+ 490
H.p.l.c. $R_t$ 2.36 min.

EXAMPLE 13

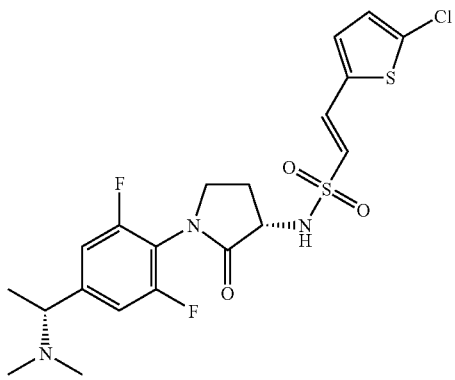

(E)-2-(5-Chloro-2-thienyl)-N-((3S)-1-{4-[(1S)-1-(dimethylamino)ethyl]-2,6-difluorophenyl}-2-oxo-3-pyrrolidinyl)ethenesulfonamide

GSK397418A

The title compound was prepared in the same way as Example 12 except using (S)-1-phenylethylamine in the formation of Intermediate 25.

Mass spectrum: Found: MH+ 490
H.p.l.c. $R_t$ 2.40 min

EXAMPLE 14

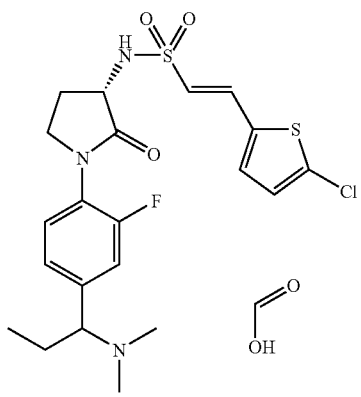

(E)-2-(5-Chloro-2-thienyl)-N-((3S)-1-{4-[1-(dimethylamino)propyl]-2-fluorophenyl}-2-oxo-3-pyrrolidinyl)ethenesulfonamide formate

GSK268880A

Intermediate 33 (0.031 g) in a mixture of trifluoroacetic acid (3 ml) and DCM (7 ml) was allowed to stand at ambient temperature for 2 h. The reaction was concentrated under reduced pressure to give a residue which was dissolved in dry MeCN (1 ml). The resultant solution was treated with DIPEA (0.068 ml) and (E)-2-(5-chloro-2-thienyl)ethenesulfonyl chloride (0.023 g) and then stirred at ambient temperature overnight. Solvent was removed under reduced pressure. The residue was purified by mass directed preparative h.p.l.c. to give the title compound (0.01 g).

Mass spectrum: Found: MH+ 486
H.p.l.c. $R_t$ 3.50 min

Example 15

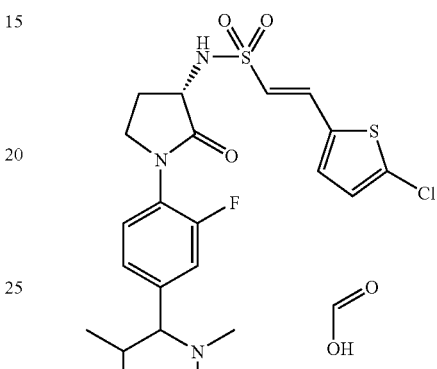

(E)-2-(5-Chloro-2-thienyl)-N-((3S)-1-{4-[1-(dimethylamino)-2-methylpropyl]-2-fluorophenyl}-2-oxo-3-pyrrolidinyl)ethenesulfonamide formate

GSK268458A

The title compound was prepared using Intermediate 35 and the procedure described for Example 14.

Mass spectrum: Found: MH+ 500
H.p.l.c. $R_t$ 2.55 min

Example 16

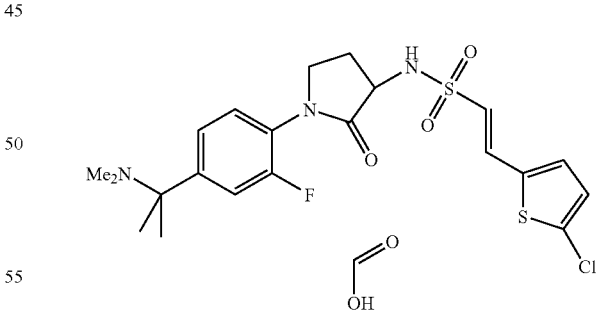

(E)-2-(5-Chloro-2-thienyl)-N-(1-{4-[1-(dimethylamino)-1-methylethyl]-2-fluorophenyl}-2-oxo-3-pyrrolidinyl)ethenesulfonamide formate

GSK3091 77A

Hydrogen chloride gas was bubbled through a suspension of zinc chloride (1.5 g) in anhydrous DCM (30 ml) at 0° C. for 30 min. Intermediate 37 (1.0 g) was added as a anhydrous DCM solution (15 ml), and HCl gas addition was continued for a further 30 min. The reaction was then filtered, and the mixture concentrated under reduced pressure. The residue was treated with dimethylamine (9 ml of a 2M solution in THF) and the resulting mixture heated to 75° C. overnight in a sealed tube. Following cooling to room temperature, the mixture was concentrated under reduced pressure, and the residue partitioned between DCM and saturated aqueous sodium bicarbonate. The organic layer was separated, reduced to minimal volume, then purified via SCX SPE chromatography, eluting with 10% methanolic ammonia. Further purification via mass directed preparative h.p.l.c. gave the title compound (4 mg).

Mass spectrum: Found: MH+ 486
H.p.l.c. $R_t$ 2.44 min

Example 17

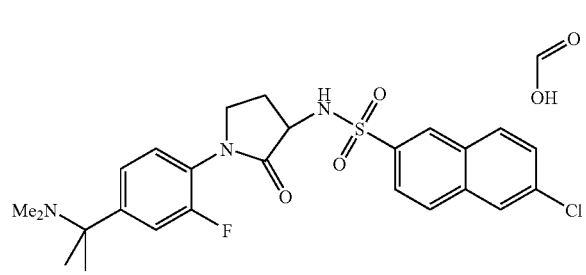

6-Chloro-N-(1-{4-[1-(dimethylamino)-1-methylethyl]-2-fluorophenyl}-2-oxo-3-pyrrolidinyl)-2-naphthalenesulfonamide formate

GSK289388A

The title compound was prepared from Intermediate 38 using the procedure described for Example 16.
Mass spectrum: Found: MH+ 504
H.p.l.c. $R_t$ 2.55 min Example 18

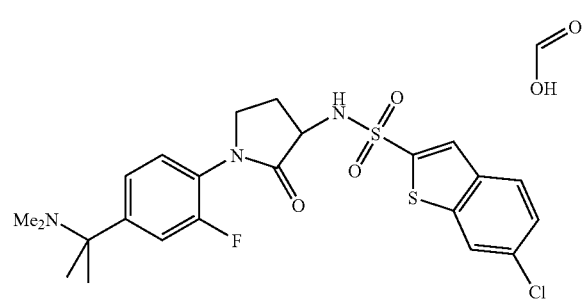

6-Chloro-N-(1-{4-[1-(dimethylamino)-1-methylethyl]-2-fluorophenyl}-2-oxo-3-pyrrolidinyl)-1-benzothiophene-2-sulfonamide formate

GSK301071A

The title compound was prepared from Intermediate 39 using the procedure described for Example 16.
Mass spectrum: Found: MH+ 510
H.p.l.c. $R_t$ 2.63 min Example 19

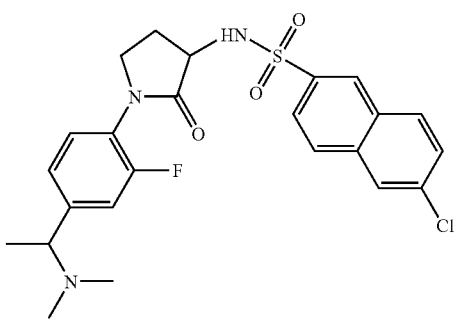

6-Chloro-N-(1-{4-[1-(dimethylamino)ethyl]-2-fluorophenyl}-2-oxo-3-pyrrolidinyl)-2-naphthalenesulfonamide A solution of Intermediate 43 (0.052 g) in dry THF (2 ml) at 0° C. under nitrogen was treated with 2N dimethylamine in THF (1 ml) and stirred for 2.5 days warming gradually to ambient temperature. The reaction was evaporated under a flow of nitrogen and the residue purified on a pre-conditioned silica SPE (10 g) eluting with 300:10:1 DCM:Methanol:0.880 Aqueous ammonia to give the title compound (0.045 g) as a white solid.

$^1$H NMR (CDCl$_3$) δ: 1.30 (3H, d), 2.18 (6H, s, 6H), 2.26 (1H, m), 2.75 (1H, m), 3.20 (1H, m), 3.69 (1H, t), 3.79 (1H, m), 3.94 (1H, m), 5.50 (1H, bs), 7.09 (2H, m), 7.26 (1H, m), 7.57 (1H, dd), 7.93 (4H, m), 8.49 (1H, s)

Example 20

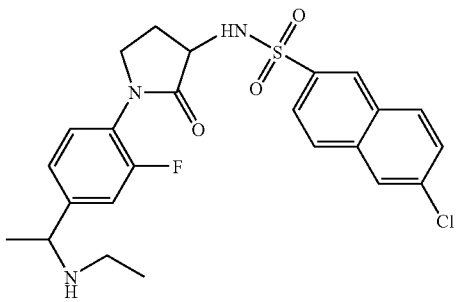

6-Chloro-N-(1-{4-[1-(ethylamino)ethyl]-2-fluorophenyl}-2-oxo-3-pyrrolidinyl)-2-naphthalenesulfonamide The title compound was prepared from Intermediate 43 and 2M ethylamine in THF using the procedure described for Example 19.
Mass spectrum: Found: MH+ 490
H.p.l.c. $R_t$ 2.56 min,
$^1$H NMR (CDCl$_3$) δ: 1.07 (3H, t), 1.31 (3H, d), 2.26 (1H, m), 2.42–2.57 (2H, m), 2.75 (1H, m), 3.68 (1H, m), 3.77

(2H, m), 3.93 (1H, m) 7.12 (2H, m), 7.26 (1H, m), 7.57 (1H, dd), 7.93 (4H, m), 8.49 (1H, s)

Example 21

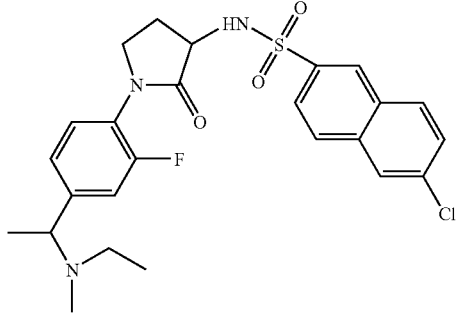

6-Chloro-N-[1-(4-{1-[ethyl(methyl)amino]ethyl}-2-fluorophenyl)-2-oxo-3-pyrrolidinyl]-2-naphthalenesulfonamide The title compound was prepared from Intermediate 43 and ethylmethylamine using the procedure described for Example 19.

Mass spectrum: Found: MH+ 504

H.p.l.c. $R_t$ 2.55 min $^1$H NMR (CDCl$_3$) δ: 1.02 (3H, bm), 1.30 (3H, bm), 2.18 (3H, bs), 2.26 (1H, m), 2.35 (1H, bm), 2.49 (1H, bm), 2.75 (1H, m), 3.52 (1H, bm), 3.69 (1H, m), 3.78 (1H, m), 3.94 (1H, m), 5.45 (1H, bm), 7.12 (2H, m), 7.26 (1H, m), 7.57 (1H, dd), 7.93 (4H, m), 8.49 (1H, s)

Example 22

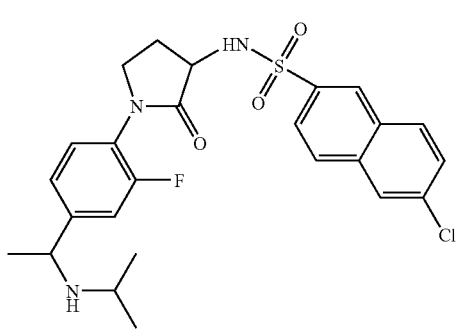

6-Chloro-N-[1-(2-fluoro-4-{1-[(1-methylethyl)amino]ethyl}phenyl)-2-oxo-3-pyrrolidinyl]-2-naphthalenesulfonamide The title compound was prepared from Intermediate 43 and (1-methylethyl)amine using the procedure described for Example 19.

Mass spectrum: Found: MH+ 504

H.p.l.c. $R_t$ 2.59 min $^1$H NMR (CDCl$_3$) δ: 1.00 (6H, m), 1.30 (3H, d), 2.27 (1H, m), 2.61 (1H, m), 2.75 (1H, m), 3.68 (1H, m), 3.79 (1H, m), 3.91 (2H, m), 7.12 (2H, m), 7.26 (1H, m), 7.57 (1H, dd), 7.93 (4H, m), 8.49 (1H, s)

Example 23

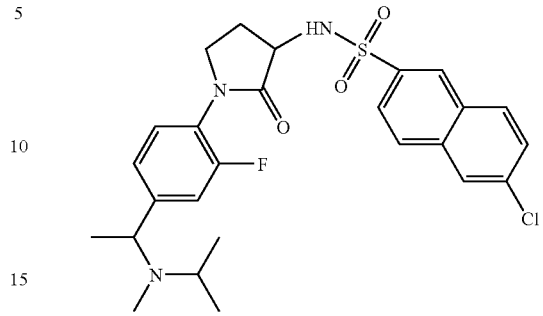

6-Chloro-N-[1-(2-fluoro-4-{1-[methyl(1-methylethyl)amino]ethyl}phenyl)-2-oxo-3-pyrrolidinyl]-2-naphthalenesulfonamide The title compound was prepared from Intermediate 43 and methyl(1-methylethyl)amine using the procedure described for Example 19.

Mass spectrum: Found: MH+ 518

H.p.l.c. $R_t$ 2.58 min $^1$H NMR (CDCl$_3$) δ: 1.14 (3H, d), 2.02 (2H, m), 2.26 (1H, m), 2.74 (1H, m), 3.13 (4H, m), 3.24 (1H, m), 3.68 (1H, m), 3.78 (1H, m), 3.93 (1H, m), 5.45 (1H, bs), 7.12 (2H, m), 7.26 (m, 1H), 7.57 (1H, dd), 7.93 (4H, m), 8.49 (1H, s)

Example 24

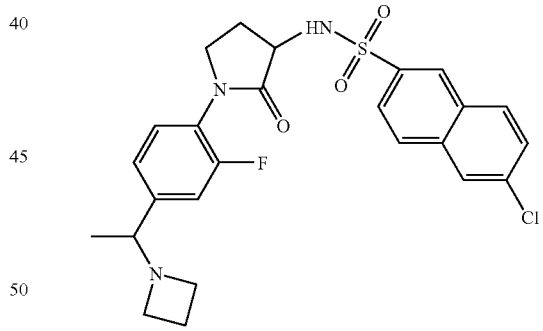

N-(1-{4-[1-(1-Azetidinyl)ethyl]-2-fluorophenyl}-2-oxo-3-pyrrolidinyl)-6-chloro-2-naphthalenesulfonamide The title compound was prepared from Intermediate 43 and azetidine using the procedure described for Example 19.

Mass spectrum: Found: MH+ 502

H.p.l.c. $R_t$ 2.55 min $^1$H NMR (CDCl$_3$) δ: 0.95 (6H, m), 1.26 (3H, d), 2.10 (3H, s), 2.26 (1H, m), 2.75 (1H, m), 2.90 (1H, m), 3.59 (1H, m), 3.68 (1H, m), 3.79 (1H, m), 3.93 (1H, m), 7.10 (2H, m), 7.24 (m, 1H), 7.58 (1H, dd), 7.93 (4H, m), 8.49 (1H, s)

Example 25

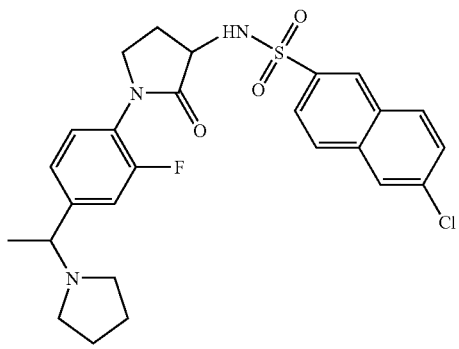

6-Chloro-N-(1-{2-fluoro-4-[1-(1-pyrrolidinyl)ethyl]phenyl}-2-oxo-3-pyrrolidinyl)-2-naphthalenesulfonamide The title compound was prepared from Intermediate 43 and pyrrolidine using the procedure described for Example 19.
Mass spectrum: Found: MH⁺ 516
H.p.l.c. $R_t$ 2.65 min
$^1$H NMR (CDCl$_3$) δ: 1.35 (3H, d), 1.76 (4H, bm), 2.26 (1H, m), 2.38 (2H, bm), 2.51 (2H, bm), 2.74 (1H, m), 3.17 (1H, m), 3.68 (1H, m), 3.79 (1H, m), 3.93 (1H, m), 5.45 (1H, bs), 7.13 (2H, m), 7.24 (1H, m), 7.58 (1H, dd), 7.93 (4H, m), 8.49 (1H, s)

Example 26

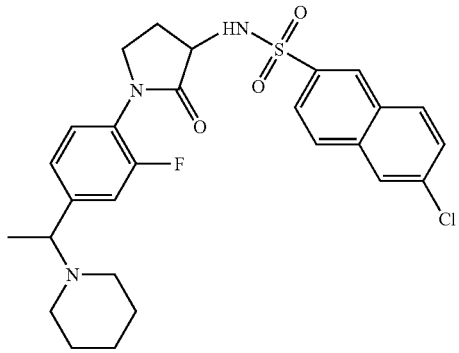

6-Chloro-N-(1-{2-fluoro-4-[1-(1-piperidinyl)ethyl]phenyl}-2-oxo-3-pyrrolidinyl)-2-naphthalenesulfonamide The title compound was prepared from Intermediate 43 and piperidine using the procedure described for Example 19.
Mass spectrum: Found: MH⁺ 530
H.p.l.c. $R_t$ 2.68 min
$^1$H NMR (CDCl$_3$) δ: 1.29 (3H, d), 1.38 (2H, m), 1.54 (4H, m), 2.21–2.42 (5H, bm), 2.75 (1H, m), 3.35 (1H, m), 3.67 (1H, m), 3.79 (1H, m), 3.93 (1H, m), 5.45 (1H, bs), 7.11 (2H, m), 7.23 (1H, m), 7.58 (1H, dd), 7.93 (4H, m), 8.49 (1H, s).

Example 27

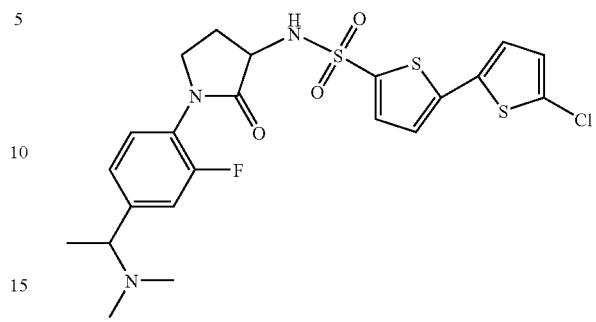

5'-Chloro-N-((3S)-1-{4-[1-(dimethylamino)ethyl]-2-fluorophenyl}-2-oxo-3-pyrrolidinyl)-2,2'-bithiophene-5-sulfonamide The title compound was prepared from Intermediate 6 and 5'-chloro-2,2'-bithiophene-5-sulfonyl chloride using the procedure described for Example 1.
Mass spectrum: Found: MH⁺ 528
H.p.l.c. $R_t$ 2.66 min

Example 28

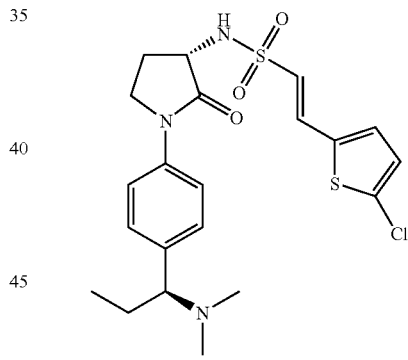

(E)-2-(5-Chloro-2-thienyl)-N-((3S)-1-{4-[(1S)-1-(dimethylamino)ethyl]phenyl}-2-oxo-3-pyrrolidinyl)ethenesulfonamide formate GSK327023A)
The title compound was prepared from Intermediate 48 and (E)-2-(5-chloro-2-thienyl)ethenesulfonyl chloride using the procedure described for Example 6 followed by purification using mass directed preparative h.p.l.c.
Mass spectrum: Found: MH⁺ 454
H.p.l.c. $R_t$ 2.39 min
$^1$H NMR (MeOD-d$_3$) 1.70 (3H, d), 2.08 (1H, m), 2.63 (1H, m), 2.72 (6H, s), 3.85 (2H, m), 4.33 (1H, m), 4.40 (1H, m), 6.91 (1H, d), 7.00 (1H, d), 7.22 (1H, d), 7.50 (1H, d), 7.52 (2H, d) 7.79 (2H, d), 8.40 (1H, bs)

Example 29

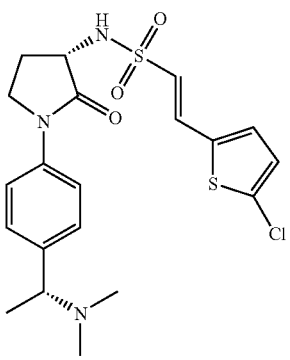

(E)-2-(5-Chloro-2-thienyl)-N-((3S)-1-{4-[(1R)-1-(dimethylamino)ethyl]phenyl}-2-oxo-3-pyrrolidinyl)ethenesulfonamide formate (GSK319326A)

The title compound was prepared from Intermediate 49 and (E)-2-(5-chloro-2-thienyl)ethenesulfonyl chloride using the procedure described for Example 6 followed by purification using mass directed preparative h.p.l.c.

Mass spectrum: Found: MH$^+$ 454

H.p.l.c. R$_t$ 2.38 min $^1$H NMR (MeOD-d$_3$) 1.70 (3H, d), 2.08 (1H, m), 2.63 (1H, m), 2.74 (6H, s), 3.85 (2H, m), 4.33 (1H, m), 4.43 (1H, m), 6.91 (1H, d), 7.00 (1H, d), 7.22 (1H, d), 7.50 (1H, d), 7.52 (2H, d) 7.79 (2H, d), 8.37 (1H, bs)

Example 30

(GSK324496A)

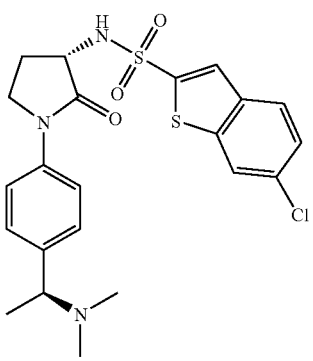

6-Chloro-N-((3S)-1-{4-[(1S)-1-(dimethylamino)ethyl]phenyl}-2-oxo-3-pyrrolidinyl)-1-benzothiophene-2-sulfonamide formate The title compound was prepared from Intermediate 48 and 6-chloro-1-benzothiophene-2-sulfonyl chloride using the procedure described for Example 8 followed by purification using mass directed preparative h.p.l.c.

Mass spectrum: Found: MH$^+$ 478

H.p.l.c. R$_t$ 2.58 min $^1$H NMR (MeOD-d$_3$) 1.69 (3H, d), 1.99 (1H, m), 2.51 (1H, m), 2.73 (6H, s), 3.80 (2H, m), 4.41 (2H, m), 7.46 (1H, m), 7.49 (2H, d), 7.74 (2H, d), 7.92 (1H, d), 8.01 (2H, m), 8.31 (1H, bs)

Example 31

(GSK319341A)

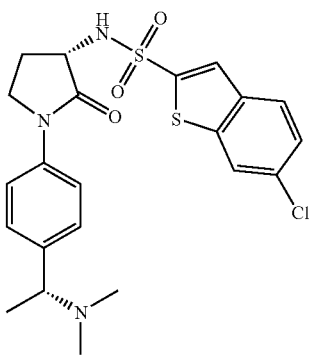

6-Chloro-N-((3S)-1-{4-[(1R)-1-(dimethylamino)ethyl]phenyl}-2-oxo-3-pyrrolidinyl)-1-benzothiophene-2-sulfonamide formate The title compound was prepared from Intermediate 49 and 6-chloro-1-benzothiophene-2-sulfonyl chloride using the procedure described for Example 8 followed by purification using mass directed preparative h.p.l.c.

Mass spectrum: Found: MH$^+$ 478

H.p.l.c. R$_t$ 2.58 min $^1$H NMR (MeOD-d$_3$) 1.69 (3H, d), 2.01 (1H, m), 2.51 (1H, m), 2.72 (6H, s), 3.80 (2H, m), 4.42 (2H, m), 7.47 (1H, m), 7.49 (2H, d), 7.74 (2H, d), 7.91 (1H, d), 8.01 (2H, m), 8.37 (1H, bs)

Example 32

(GSK259556A)

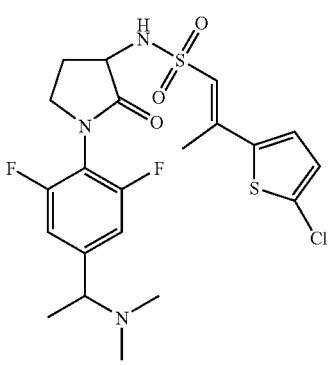

(1E)-2-(5-Chloro-2-thienyl)-N-(1-{4-[1-(dimethylamino)ethyl]-2,6-difluorophenyl}-2-oxo-3-pyrrolidinyl)-1-propene-1-sulfonamide formate The title compound was prepared using Intermediate 55 and (1E)-2-(5-chloro-2-thienyl)-1-propene-1-sulfonyl chloride using the procedure described for Example 6, followed by purification using mass directed preparative h.p.l.c.

Mass spectrum: Found: MH+ 504

H.p.l.c. $R_t$ 2.49 min $^1$H NMR (MeOD-d$_3$) δ 1.65 (3H, d), 2.21 (1H, m), 2.47 (3H, d), 2.67 (1H, m), 2.72 (6H, s), 3.70 (1H, bm), 3.79 (1H, m), 4.33 (1H, bm), 4.46 (1H, dd), 6.93 (1H, bm), 6.97 (1H, d), 7.26 (1H, d), 7.31 (2H, bm), 8.19 (1H, bs)

Example 33

6-Chloro-N-(1-{4-[1-(dimethylamino)ethyl]-2,6-difluorophenyl}-2-oxo-3-pyrrolidinyl)-1-benzothiophene-2-sulfonamide formate (GSK259555A)

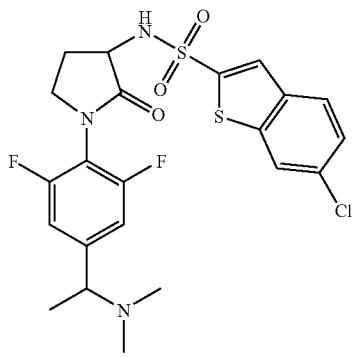

The title compound was prepared from Intermediate 55 and 6-chloro-1-benzothiophene-2-sulfonyl chloride using the procedure described for Example 8 followed by purification using mass directed preparative h.p.l.c.

Mass spectrum: Found: MH+ 514

H.p.l.c. $R_t$ 2.57 min $^1$H NMR (MeOD-d$_3$) δ 1.65 (3H, m), 2.12 (1H, m), 2.55 (1H, m), 2.72 (6H, s), 3.64 (1H, bm), 3.73 (1H, m), 4.38 (1H, bm), 4.48 (1H, dd), 7.31 (2H, bm), 7.45 (1H, d), 7.91 (1H, d), 8.00 (2H, bm), 8.20 (1H, bs)

In vitro Assay for Inhibition of Factor Xa

Compounds of the present invention were tested for their Factor Xa inhibitory activity as determined in vitro by their ability to inhibit human Factor Xa in a fluorogenic assay, using Rhodamine 110, bis-CBZ-glycylglycyl-L-arginine amide as the fluorogenic substrate. Compounds were diluted from a 10 mM stock solution in dimethylsulfoxide at appropriate concentrations. Assay was performed at room temperature using buffer consisting of: 50 mM Tris-HCl, 150 mM NaCl, 5 mM CaCl$_2$, pH 7.4 containing human Factor Xa (final concentration of 0.0003 U.ml-1). Compound and enzyme were preincubated for 15 min prior to addition of the substrate (final concentration of 10 μM). The reaction was stopped after 3 hrs with the addition of H-D-Phe-Pro-Arg-Chloromethylketone. An LJL-Analyst fluorimeter was used to monitor fluorescence with 485 nm excitation/535 nm emission. To obtain IC$_{50}$ values the data were analysed using ActivityBase® and XLfit®.

Calculation of Ki values:

Ki =IC$_{50}$/(1+[Substrate]/Km)

The Ki value for the above assay can be obtained by dividing the IC$_{50}$ value by 1.6.

All of the synthetic Example compounds tested by the above described in vitro assay were found to exhibit Factor Xa inhibitory activity. Preferably, compounds have a Ki value of less than 1 μM. More preferably, compounds have a Ki value of less than 0.1 μM. Most preferably, compounds have a Ki value of less than 10 nM (e.g. Examples 1–18).

Method for Measurement of Prothrombin Time (PT)

Blood was collected into a sodium citrate solution (ratio 9:1) to give a final concentration of 0.38% citrate. Plasma was generated by centrifugation of citrated blood samples at 1200×g for 20 min at 4° C. and stored at −20° C. until use. PT analysis was conducted using plasma pooled from 4 separate donors (2 male and 2 female).

The PT test was performed using the BCS Coagulation Analyzer (Dade Behring). For assay, 50 ul of plasma containing test compound at concentrations ranging from 0.03 to 100 uM (made from a 100 uM stock containing 1% DMSO in plasma) was combined with 100 ul of Thromboplastin C Plus (Dade Behring). Upon addition of the reagents, absorbance at 405 nm was monitored and time to clot formation is determined (normal range for human plasma is 10.6–12.4 seconds).

All of the synthetic Example compounds tested by the above described assay were found to exhibit activity.

General Purification and Analytical Methods

LC/MS Method

Analytical HPLC was conducted on a Supelcosil LCABZ+PLUS column (3 μm, 3.3 cm×4.6 mm ID) eluting with 0.1% HCO$_2$H and 0.1M ammonium acetate in water (solvent A), and 95% MeCN and 0.05% HCO$_2$H in water (solvent B), using the following elution gradient 0–0.7 min 0% B, 0.74–4.2 min →100% B, 4.2–5.3 min 100% B, 5.3–5.5 min 100→0% B at a flow rate of 3 ml/min (System 1). The mass spectra (MS) were recorded on a Fisons VG Platform mass spectrometer using electrospray positive ionisation. [(ES+ve to give MH+ and M(NH$_4$)+ molecular ions] or electrospray negative ionisation [(ES-ve to give (M−H)− molecular ion] modes.

$^1$H nmr spectra were recorded using a Bruker DPX 400 MHz spectrometer, using tetramethylsilane as the external standard.

Biotage™ chromatography refers to purification carried out using equipment sold by Dyax Corporation (either the Flash 40i or Flash 150i) and cartridges pre-packed with KPSil™.

Mass directed preparative h.p.l.c. refers to methods where the material was purified by high performance liquid chromatography on a HPLCABZ+ 5 μm column (5 cm×10 mm internal diameter) with 0.1% HCO$_2$H in water and 95% MeCN, 5% water (0.5% HCO$_2$H) utilising the following gradient elution conditions: 0–1.0 min 5% B, 1.0–8.0 min 5→30% B, 8.0–8.9 min 30% B, 8.9–9.0 min 30→95% B, 9.0–9.9 min 95% B, 9.9–10 min 95→0% B at a flow rate of 8 ml min$^{-1}$ (System 2). The Gilson 202-fraction collector was triggered by a VG Platform Mass Spectrometer on detecting the mass of interest.

Hydrophobic frits refers to filtration tubes sold by Whatman.

SPE (solid phase extraction) refers to the use of cartridges sold by International Sorbent Technology Ltd. Silica SPE and SCX SPE were used.

The internal diameter of the Chiralpak OD and Chiralcel OJ columns is 0.46×25 cm RediSep™ silica refers to pre-packed silica cartridges sold by ISCO Inc.

Combi Flash® Companion™ refers to an automated purification system sold by ISCO Inc.

What is claimed is:

1. A compound of formula (I):

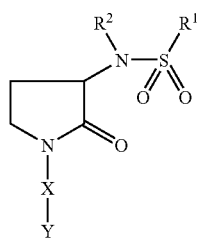

wherein:

R¹ represents a group selected from:

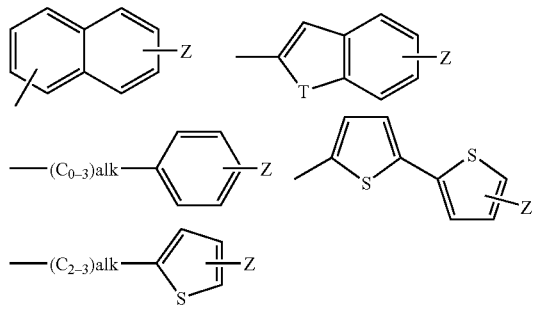

each ring of which optionally includes a further heteroatom N,

Z represents an optional substituent halogen, alk represents alkylene or alkenylene, T represents S, O or NH;

R² represents hydrogen, —$C_{1-6}$alkyl, —$C_{1-3}$alkylCON-$R^aR^b$, —$C_{1-3}$alkylCO$_2C_{1-4}$alkyl, —CO$_2C_{1-4}$alkyl or —$C_{1-3}$alkylCO$_2$H;

$R^a$ and $R^b$ independently represent hydrogen, —$C_{1-6}$alkyl, or together with the N atom to which they are bonded form a 5-, 6- or 7-membered non-aromatic heterocyclic ring optionally containing an additional heteroatom selected from O, N or S(O)$_n$, optionally substituted by $C_{1-4}$alkyl;

n represents 0–2;

X represents phenyl or a 5- or 6-membered aromatic heterocyclic group consisting of at least one heteroatom selected from O, N or S, each of which is optionally substituted by 0–2 groups selected from: halogen, —$C_{1-4}$alkyl, —$C_{2-4}$alkenyl, —CN, —CF$_3$, —NR$^a$R$^b$, —$C_{0-4}$alkylOR$^e$, —C(O)R$^f$ and —C(O)NR$^a$R$^b$;

$R^e$ represents hydrogen or —$C_{1-6}$alkyl;

$R^f$ represents —$C_{1-6}$alkyl;

Y represents a group —C(R$^x$)(R$^z$)C$_{0-2}$alkylNR$^c$R$^d$;

$R^x$ represents $C_{1-4}$alkyl optionally substituted by halogen;

$R^z$ represents hydrogen or $C_{1-4}$alkyl optionally substituted by halogen;

$R^c$ and $R^d$ independently represent hydrogen, —$C_{1-6}$alkyl, —$C_{1-4}$alkylOH, or together with the N atom to which they are bonded form a 4-, 5-, 6- or 7-membered non-aromatic heterocyclic ring, the 5-, 6- or 7-membered non-aromatic heterocyclic ring optionally consisting of an additional heteroatom selected from O, N or S, optionally substituted by $C_{1-4}$alkyl.

2. A compound according to claim 1 wherein R¹ represents a group selected from:

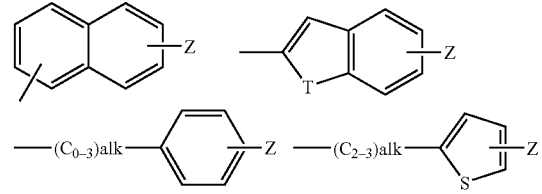

each ring of which optionally includes a further heteroatom N,

Z represents an optional substituent halogen, alk represents alkylene or alkenylene, T represents S, O or NH.

3. A compound according to claim 1 wherein R² represents hydrogen.

4. A compound according to claim 1 wherein X represents phenyl or a 5- or 6-membered aromatic heterocyclic group consisting of at least one heteroatom selected from O, N or S, each of which is optionally substituted by 0–2 groups selected from: halogen, —$C_{1-4}$alkyl and —NR$^a$R$^b$.

5. A compound according to claim 1 wherein Y represents a group —C(R$^x$)(R$^z$)NR$^c$R$^d$.

6. A compound according to claim 1 wherein R¹ represents a group selected from:

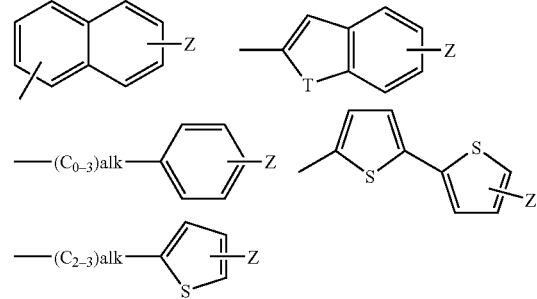

each ring of which optionally includes a further heteroatom N,

Z represents an optional substituent halogen, alk represents alkylene or alkenylene, T represents S, O or NH;

R² represents hydrogen, —$C_{1-6}$alkyl, —$C_{1-3}$alkylCON-$R^aR^b$, —$C_{1-3}$alkylCO$_2C_{1-4}$alkyl, —CO$_2C_{1-4}$alkyl or —$C_{1-3}$alkylCO$_2$H;

$R^a$ and $R^b$ independently represent hydrogen, —$C_{1-6}$alkyl, or together with the N atom to which they are bonded form a 5-, 6- or 7-membered non-aromatic heterocyclic ring optionally consisting of an additional heteroatom selected from O, N or S(O)$_n$, optionally substituted by $C_{1-4}$alkyl;

X represents phenyl or a 5- or 6-membered aromatic heterocyclic group consisting of at least one heteroatom selected from O, N or S, each of which is optionally substituted by 0–2 groups selected from: halogen, —$C_{1-4}$alkyl, —$C_{2-4}$alkenyl, —CN, —CF$_3$, —NR$^a$R$^b$, —$C_{0-4}$alkylOR$^e$, —C(O)R$^f$ and —C(O)NR$^a$R$^b$;

$R^e$ represents hydrogen or —$C_{1-6}$alkyl;
$R^f$ represents —$C_{1-6}$alkyl;
Y represents a group —$C(R^x)(R^z)C_{0-2}$alkyl$NR^cR^d$;
$R^x$ represents $C_{1-4}$alkyl optionally substituted by halogen;
$R^z$ represents hydrogen or $C_{1-4}$alkyl optionally substituted by halogen;
$R^c$ and $R^d$ independently represent hydrogen, —$C_{1-6}$alkyl, —$C_{1-4}$alkylOH, or together with the N atom to which they are bonded form a 5- or 6-membered non-aromatic heterocyclic ring optionally containing an additional heteroatom selected from O, N or S, optionally substituted by $C_{1-4}$alkyl.

7. A compound selected from:
(E)-2-(5-Chloro-2-thienyl)-N-(1-{4-[1-(dimethylamino)ethyl]-2-fluorophenyl}-2-oxo-3-pyrrolidinyl)ethenesulfonamide;
(E)-2-(5-Chloro-2-thienyl)-N-(1-{2-fluoro-4-[1-(4-morpholinyl)ethyl]phenyl}-2-oxo-3-pyrrolidinyl)ethenesulfonamide;
(E)-2-(5-Chloro-2-thienyl)-N-[1-(2-fluoro-4-{1-[(2-hydroxyethyl)(methyl)amino]ethyl}phenyl)-2-oxo-3-pyrrolidinyl]ethenesulfonamide;
(E)-N-{1-[4-(1-Aminoethyl)-2-fluorophenyl]-2-oxo-3-pyrrolidinyl}-2-(5-chloro-2-thienyl)ethenesulfonamide;
6-Chloro-N-(1-{4-[1-(dimethylamino)ethyl]-2-fluorophenyl}-2-oxo-3-pyrrolidinyl)-1-benzothiophene-2-sulfonamide;
(E)-2-(5-Chloro-2-thienyl)-N-((3S)-1-{4-[(1S)-1-(dimethylamino)ethyl]-2-fluorophenyl}-2-oxo-3-pyrrolidinyl)ethenesulfonamide;
6-Chloro-N-((3S)-1-{4-[(1S)-1-(dimethylamino)ethyl]-2-fluorophenyl}-2-oxo-3-pyrrolidinyl)-2-naphthalenesulfonamide;
6-Chloro-N-((3S)-1-{4-[(1S)-1-(dimethylamino)ethyl]-2-fluorophenyl}-2-oxo-3-pyrrolidinyl)-1-benzothiophene-2-sulfonamide;
(E)-2-(5-Chloro-2-thienyl)-N-((3S)-1-{4-[(1R)-1-(dimethylamino)ethyl]-2-fluorophenyl}-2-oxo-3-pyrrolidinyl)ethenesulfonamide;
6-Chloro-N-((3S)-1-{4-[(1R)-1-(dimethylamino)ethyl]-2-fluorophenyl}-2-oxo-3-pyrrolidinyl)-2-naphthalenesulfonamide;
6-Chloro-N-((3S)-1-{4-[(1R)-1-(dimethylamino)ethyl]-2-fluorophenyl}-2-oxo-3-pyrrolidinyl)-1-benzothiophene-2-sulfonamide;
(E)-2-(5-Chloro-2-thienyl)-N-((3S)-1-{4-[(1R)-1-(dimethylamino)ethyl]-2,6-difluorophenyl}-2-oxo-3-pyrrolidinyl)ethenesulfonamide;
(E)-2-(5-Chloro-2-thienyl)-N-((3S)-1-{4-[(1S)-1-(dimethylamino)ethyl]-2,6-difluorophenyl}-2-oxo-3-pyrrolidinyl)ethenesulfonamide;
(E)-2-(5-Chloro-2-thienyl)-N-((3S)-1-{4-[1-(dimethylamino)propyl]-2-fluorophenyl}-2-oxo-3-pyrrolidinyl)ethenesulfonamide;
(E)-2-(5-Chloro-2-thienyl)-N-((3S)-1-{4-[1-(dimethylamino)-2-methylpropyl]-2-fluorophenyl}-2-oxo-3-pyrrolidinyl)ethenesulfonamide;
(E)-2-(5-Chloro-2-thienyl)-N-(1-{4-[1-(dimethylamino)-1-methylethyl]-2-fluorophenyl}-2-oxo-3-pyrrolidinyl)ethenesulfonamide;
6-Chloro-N-(1-{4-[1-(dimethylamino)-1-methylethyl]-2-fluorophenyl}-2-oxo-3-pyrrolidinyl)-2-naphthalenesulfonamide;
6-Chloro-N-(1-{4-[1-(dimethylamino)-1-methylethyl]-2-fluorophenyl}-2-oxo-3-pyrrolidinyl)-1-benzothiophene-2-sulfonamide;
6-Chloro-N-(1-{4-[1-(dimethylamino)ethyl]-2-fluorophenyl}-2-oxo-3-pyrrolidinyl)-2-naphthalenesulfonamide;
6-Chloro-N-(1-{4-[1-(ethylamino)ethyl]-2-fluorophenyl}-2-oxo-3-pyrrolidinyl)-2-naphthalenesulfonamide;
6-Chloro-N-[1-(4-{1-[ethyl(methyl)amino]ethyl}-2-fluorophenyl)-2-oxo-3-pyrrolidinyl]-2-naphthalenesulfonamide;
6-Chloro-N-[1-(2-fluoro-4-{1-[(1-methylethyl)amino]ethyl}phenyl)-2-oxo-3-pyrrolidinyl]-2-naphthalenesulfonamide;
6-Chloro-N-[1-(2-fluoro-4-{1-[methyl(1-methylethyl)amino]ethyl}phenyl)-2-oxo-3-pyrrolidinyl]-2-naphthalenesulfonamide;
N-(1-{4-[1-(1-Azetidinyl)ethyl]-2-fluorophenyl}-2-oxo-3-pyrrolidinyl)-6-chloro-2-naphthalenesulfonamide;
6-Chloro-N-(1-{2-fluoro-4-[1-(1-pyrrolidinyl)ethyl]phenyl}-2-oxo-3-pyrrolidinyl)-2-naphthalenesulfonamide;
6-Chloro-N-(1-{2-fluoro-4-[1-(1-piperidinyl)ethyl]phenyl}-2-oxo-3-pyrrolidinyl)-2-naphthalenesulfonamide;
5'-Chloro-N-((3S)-1-{4-[1-(dimethylamino)ethyl]-2-fluorophenyl}-2-oxo-3-pyrrolidinyl)-2,2'-bithiophene-5-sulfonamide;
(E)-2-(5-Chloro-2-thienyl)-N-((3S)-1-{4-[(1S)-1-(dimethylamino)ethyl]phenyl}-2-oxo-3-pyrrolidinyl)ethenesulfonamide;
(E)-2-(5-Chloro-2-thienyl)-N-((3S)-1-{4-[(1R)-1-(dimethylamino)ethyl]phenyl}-2-oxo-3-pyrrolidinyl)ethenesulfonamide;
6-Chloro-N-((3S)-1-{4-[(1S)-1-(dimethylamino)ethyl]phenyl}-2-oxo-3-pyrrolidinyl)-1-benzothiophene-2-sulfonamide;
6-Chloro-N-((3S)-1-{4-[(1R)-1-(dimethylamino)ethyl]phenyl}-2-oxo-3-pyrrolidinyl)-1-benzothiophene-2-sulfonamide;
(1E)-2-(5-Chloro-2-thienyl)-N-(1-{4-[1-(dimethylamino)ethyl]-2,6-difluorophenyl}-2-oxo-3-pyrrolidinyl)-1-propene-1-sulfonamide; and
6-Chloro-N-(1-{4-[1-(dimethylamino)ethyl]-2,6-difluorophenyl}-2-oxo-3-pyrrolidinyl)-1-benzothiophene-2-sulfonamide.

8. A pharmaceutical composition comprising a compound according to claim 1 together with at least one pharmaceutical carrier or excipient.

* * * * *